(12) United States Patent
Guillemont et al.

(10) Patent No.: US 11,179,396 B2
(45) Date of Patent: Nov. 23, 2021

(54) HETEROCYCLIC COMPOUNDS AS ANTIBACTERIALS

(71) Applicant: Janssen Sciences Ireland Unlimited Company, County Cork (IE)

(72) Inventors: Jérôme Émile Georges Guillemont, Andé (FR); Pierre Jean-Marie Bernard Raboisson, Wavre (BE); Abdellah Tahri, Anderlecht (BE)

(73) Assignee: Janssen Sciences Ireland UC, County Cork (IE)

( * ) Notice: Subject to any disclaimer, the term of this patent is extended or adjusted under 35 U.S.C. 154(b) by 0 days.

(21) Appl. No.: 16/309,725

(22) PCT Filed: Jun. 15, 2017

(86) PCT No.: PCT/EP2017/064652
§ 371 (c)(1),
(2) Date: Dec. 13, 2018

(87) PCT Pub. No.: WO2017/216281
PCT Pub. Date: Dec. 21, 2017

(65) Prior Publication Data
US 2019/0134046 A1    May 9, 2019

(30) Foreign Application Priority Data
Jun. 16, 2016  (EP) .................................. 16174719

(51) Int. Cl.
| A61K 31/519 | (2006.01) |
| A61K 45/06 | (2006.01) |
| C07D 471/04 | (2006.01) |
| C07D 487/04 | (2006.01) |
| C07D 513/04 | (2006.01) |
| A61P 31/06 | (2006.01) |
| A61K 31/429 | (2006.01) |
| A61K 31/437 | (2006.01) |

(52) U.S. Cl.
CPC .......... *A61K 31/519* (2013.01); *A61K 31/429* (2013.01); *A61K 31/437* (2013.01); *A61K 45/06* (2013.01); *A61P 31/06* (2018.01); *C07D 471/04* (2013.01); *C07D 487/04* (2013.01); *C07D 513/04* (2013.01)

(58) Field of Classification Search
CPC .................................................... A61K 31/519
See application file for complete search history.

(56) References Cited

U.S. PATENT DOCUMENTS

| 6,090,820 A | 7/2000 | Barbachyn et al. |
| 8,304,419 B2 | 11/2012 | Chong et al. |
| 9,029,389 B2 | 5/2015 | No et al. |
| 10,155,756 B2 | 12/2018 | Lu et al. |
| 2011/0183342 A1 | 7/2011 | Lewinsohn et al. |
| 2014/0073622 A1 | 3/2014 | Soneda et al. |
| 2016/0318925 A1 | 11/2016 | Miller et al. |
| 2017/0313697 A1 | 11/2017 | Lu et al. |

FOREIGN PATENT DOCUMENTS

| JP | 2011046745 | 3/2011 | |
| KR | 1999/008399 | 1/1999 | |
| KR | 2014/0011017 | 1/2014 | |
| KR | 2014/0065902 | 5/2014 | |
| KR | 2015/0060224 | 6/2015 | |
| MA | 27360 | 6/2005 | |
| WO | WO 1996/15130 | 5/1996 | |
| WO | WO 2004/011436 | 2/2004 | |
| WO | 2005/012292 | 2/2005 | |
| WO | 2008/082490 | 7/2008 | |
| WO | WO 2009/120789 | 10/2009 | |
| WO | WO 2010/078408 | 8/2010 | |
| WO | WO 2011/057145 | 5/2011 | |
| WO | WO 2011/113606 | 9/2011 | |
| WO | WO-2011113606 A1 * | 9/2011 | ........... A61K 31/437 |
| WO | WO 2013/033070 | 3/2013 | |
| WO | WO 2013/033167 | 3/2013 | |
| WO | WO 2013/127269 | 9/2013 | |
| WO | WO 2014/015167 | 1/2014 | |
| WO | WO 2015/014993 | 2/2015 | |
| WO | WO 2016/062151 | 4/2016 | |
| WO | 2016/073524 | 5/2016 | |
| WO | WO 2017/001660 | 1/2017 | |
| WO | WO 2017/001661 | 1/2017 | |
| WO | WO 2017/216281 | 12/2017 | |
| WO | WO 2017/216283 | 12/2017 | |
| WO | 2018/158280 | 9/2018 | |

OTHER PUBLICATIONS

Sunhee Kang et al., Journal of Medicinal, Chemistry—vol. 57, No. 12, pp. 5293-5305, 2014.
Bundegaard, H. "Design of Prodrugs" p. 1-92, Elesevier, New York-Oxford (1985).
Cihan-Üstündag et al, Molecular Diversity, 2012, vol. 16 (3), pp. 525-539.
Database Registry Chemical Abstract Service, RN 1783117-90-7; Jun. 18, 2015, XP 055221200.

(Continued)

*Primary Examiner* — John S Kenyon
(74) *Attorney, Agent, or Firm* — Sofia Kopelevich

(57) ABSTRACT

The present invention relates to the following compounds

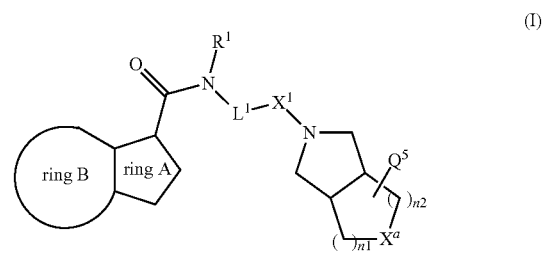

wherein the integers are as defined in the description, and where the compounds may be useful as medicaments, for instance for use in the treatment of tuberculosis.

22 Claims, No Drawings

(56) References Cited

OTHER PUBLICATIONS

Database Registry Chemical Abstract Service, RN 1156922-31-4; Jun. 14, 2009, XP055221197.
Database Registry Chemical Abstract Service, RN 1409441-72-0; Dec. 2, 2012, XP 055221191.
Database Registry Chemical Abstract Service, RN 1638404-01-9; Dec. 10, 2014, XP055221179.
Database Registry Chemical Abstract Service, RN 1394533-85-7; Sep. 18, 2012, XP 055221174.
Database Registry Chemical Abstract Service, RN 1638474-30-2; Dec. 11, 2014, XP055221208.
Güzel et al, General Papers Arkivoc 2006, xii, pp. 98-110.
Kang et al., J. Medicinal Chemistry, 2014, 57 (12), pp. 5293-5305.
Moraski et al, ACS Medicinal Chemistry Letters, vol. 4, No. 7, pp. 675-679, 2013.
Moraski et al, ACS Infectious Diseases, vol. 1, No. 2, pp. 85-90, 2015.
Ollinger et al, Plos One, vol. 8, No. 4, pp. e60531, 2013.
Pethe et al "Discovery of Q203, a potent clinical candidate for the treatment of tuberculosis", Nature Medicine, 19, 1157-1160 (2013).
Tang et al, ACS Medicinal Chemistry Letters. vol. 6, No. 7, pp. 814-818, 2015.
Tester, R. et al., Bioorganic and Medicinal Chemistry Letters 20 (2010) 2560-2563.
Tiwari et al., ACS Med Chem Lett, 2014, vol. 5, pp. 587-591.
International Search Report for PCT/EP2016/065499 dated Sep. 9, 2016.
International Search Report for PCT/EP2016/065503 dated Aug. 12, 2016.
International Search Report for PCT/EP2017/064652 dated Jul. 21, 2017.
International Search Report for PCT/EP2017/064654 dated Jul. 21, 2017.
International Search Report for PCT/EP2018/054860 dated May 28, 2018.
CAS Registry No. 1831341-34-4; STN entry date: Dec. 17, 2015; 2H-Pyrazolo[4,3-c]pyridine-3-carboxamide, N-[[4-(cyclohexylmethylamino)phenyl]methyl]-4,5,6,7-tetrahydro-, hydrochloride (1:1).
CAS Registry No. 1831341-33-3; STN entry date: Dec. 17, 2015; 2H-Pyrazolo[4,3-c]pyridine-3-carboxamide, N-[[4-(cyclohexylmethylamino)phenyl]methyl]-4,5,6,7-tetrahydro.
CAS Registry No. 1625238-97-2; STN entry date: Sep. 24, 2014; Pyrazolo[1,5-a]pyrimidine-3-carboxamide, N-[[4-(cyclohexylmethylamino)phenyl]methyl]-2-methyl.
CAS Registry No. 1320875-52-2; STN entry date: Aug. 21, 2011; Pyrazolo[1,5-a]pyrimidine-3-carboxamide, N-[[4-(cyclohexylmethylamino)phenyl]methyl]-5,7-dimethyl.
CAS Registry No. 1278717-74-0; STN entry date: Apr. 13, 2011; Pyrazolo[1,5-a]pyrimidine-3-carboxamide, N-[[4-(cyclohexylmethylamino)phenyl]methyl]-2,5,7-trimethyl.
Chetty et al., Bioorganic & Medicinal Chemistry Letters, Pergamon, Amsterdam, NL, vol. 27, No. 3, Nov. 29, 2016 (Nov. 29, 2016), pp. 370-386.
CAS Registry No. 1299681-23-4; STN Entry date May 24, 2011; Furo [2, 3-d) pyrimidine—5-carboxamide, N-[[(cyclohexylmethylamino)phenyl]methyl}-3,4-dihydro-6-methyl-4-oxo-.
CAS Registry No. 1289433-56-2; [2, STN entry date: May 3, 2011; Furo [2, 3-d] pyrimidine-5-carboxamide, N-[[4-(cyclohexylmethylamino)phenyl]methyl]-3,4-dihydro-3,6-dimethyl-4oxo-.
Gualano G et al., Infectious Disease Reports, 2016, vol. 8 (2), pp. 43-49.
Lamprecht D et al., Nature Communications, vol. 7 (1), pp. 1-14.
Zhang et al., Microbiological Spectrum, Mechanisms of Pyrazinamide Action and Resistance, vol. 2 issue 4, pp. 1-12.
Zumla A et al., The Lancet Respiratory Medicine, 2015, vol. 3(3), pp. 220-234.

\* cited by examiner

HETEROCYCLIC COMPOUNDS AS ANTIBACTERIALS

CROSS REFERENCE TO RELATED APPLICATIONS

This application is the national stage of PCT Application No. PCT/EP2017/064652, filed Jun. 15, 2017, which claims priority from European Patent Application No. 16174719.1 filed Jun. 16, 2016, the entire disclosures of which are hereby incorporated by reference in their entirety.

The present invention relates to novel compounds. The invention also relates to such compounds for use as a pharmaceutical and further for the use in the treatment of bacterial diseases, including diseases caused by pathogenic mycobacteria such as *Mycobacterium tuberculosis*. Such compounds may work by interfering with ATP synthase in *M. tuberculosis*, with the inhibition of cytochrome $bc_1$ activity as the primary mode of action. Hence, primarily, such compounds are antitubercular agents.

BACKGROUND OF THE INVENTION

*Mycobacterium tuberculosis* is the causative agent of tuberculosis (TB), a serious and potentially fatal infection with a world-wide distribution. Estimates from the World Health Organization indicate that more than 8 million people contract TB each year, and 2 million people die from tuberculosis yearly. In the last decade, TB cases have grown 20% worldwide with the highest burden in the most impoverished communities. If these trends continue, TB incidence will increase by 41% in the next twenty years. Fifty years since the introduction of an effective chemotherapy, TB remains after AIDS, the leading infectious cause of adult mortality in the world. Complicating the TB epidemic is the rising tide of multi-drug-resistant strains, and the deadly symbiosis with HIV. People who are HIV-positive and infected with TB are 30 times more likely to develop active TB than people who are HIV-negative and TB is responsible for the death of one out of every three people with HIV/AIDS worldwide.

Existing approaches to treatment of tuberculosis all involve the combination of multiple agents. For example, the regimen recommended by the U.S. Public Health Service is a combination of isoniazid, rifampicin and pyrazinamide for two months, followed by isoniazid and rifampicin alone for a further four months. These drugs are continued for a further seven months in patients infected with HIV. For patients infected with multi-drug resistant strains of *M. tuberculosis*, agents such as ethambutol, streptomycin, kanamycin, amikacin, capreomycin, ethionamide, cycloserine, ciprofoxacin and ofloxacin are added to the combination therapies. There exists no single agent that is effective in the clinical treatment of tuberculosis, nor any combination of agents that offers the possibility of therapy of less than six months' duration.

There is a high medical need for new drugs that improve current treatment by enabling regimens that facilitate patient and provider compliance. Shorter regimens and those that require less supervision are the best way to achieve this. Most of the benefit from treatment comes in the first 2 months, during the intensive, or bactericidal, phase when four drugs are given together; the bacterial burden is greatly reduced, and patients become noninfectious. The 4- to 6-month continuation, or sterilizing, phase is required to eliminate persisting bacilli and to minimize the risk of relapse. A potent sterilizing drug that shortens treatment to 2 months or less would be extremely beneficial. Drugs that facilitate compliance by requiring less intensive supervision also are needed. Obviously, a compound that reduces both the total length of treatment and the frequency of drug administration would provide the greatest benefit.

Complicating the TB epidemic is the increasing incidence of multi-drug-resistant strains or MDR-TB. Up to four percent of all cases worldwide are considered MDR-TB—those resistant to the most effective drugs of the four-drug standard, isoniazid and rifampin. MDR-TB is lethal when untreated and cannot be adequately treated through the standard therapy, so treatment requires up to 2 years of "second-line" drugs. These drugs are often toxic, expensive and marginally effective. In the absence of an effective therapy, infectious MDR-TB patients continue to spread the disease, producing new infections with MDR-TB strains. There is a high medical need for a new drug with a new mechanism of action, which is likely to demonstrate activity against drug resistant, in particular MDR strains.

The term "drug resistant" as used hereinbefore or hereinafter is a term well understood by the person skilled in microbiology. A drug resistant *Mycobacterium* is a *Mycobacterium* which is no longer susceptible to at least one previously effective drug; which has developed the ability to withstand antibiotic attack by at least one previously effective drug. A drug resistant strain may relay that ability to withstand to its progeny. Said resistance may be due to random genetic mutations in the bacterial cell that alters its sensitivity to a single drug or to different drugs.

MDR tuberculosis is a specific form of drug resistant tuberculosis due to a bacterium resistant to at least isoniazid and rifampicin (with or without resistance to other drugs), which are at present the two most powerful anti-TB drugs. Thus, whenever used hereinbefore or hereinafter "drug resistant" includes multi drug resistant.

Another factor in the control of the TB epidemic is the problem of latent TB. In spite of decades of tuberculosis (TB) control programs, about 2 billion people are infected by *M. tuberculosis*, though asymptomatically. About 10% of these individuals are at risk of developing active TB during their lifespan. The global epidemic of TB is fuelled by infection of HIV patients with TB and rise of multi-drug resistant TB strains (MDR-TB). The reactivation of latent TB is a high risk factor for disease development and accounts for 32% deaths in HIV infected individuals. To control TB epidemic, the need is to discover new drugs that can kill dormant or latent bacilli. The dormant TB can get reactivated to cause disease by several factors like suppression of host immunity by use of immunosuppressive agents like antibodies against tumor necrosis factor at or interferon-γ. In case of HIV positive patients the only prophylactic treatment available for latent TB is two-three months regimens of rifampicin, pyrazinamide. The efficacy of the treatment regime is still not clear and furthermore the length of the treatments is an important constrain in resource-limited environments. Hence there is a drastic need to identify new drugs, which can act as chemoprophylatic agents for individuals harboring latent TB bacilli.

The tubercle bacilli enter healthy individuals by inhalation; they are phagocytosed by the alveolar macrophages of the lungs. This leads to potent immune response and formation of granulomas, which consist of macrophages infected with *M. tuberculosis* surrounded by T cells. After a period of 6-8 weeks the host immune response cause death of infected cells by necrosis and accumulation of caseous material with certain extracellular bacilli, surrounded by macrophages, epitheloid cells and layers of lymphoid tissue at the periphery. In case of healthy individuals, most of the mycobacteria are killed in these environments but a small proportion of bacilli still survive and are thought to exist in a non-replicating, hypometabolic state and are tolerant to killing by anti-TB drugs like isoniazid. These bacilli can remain in the altered physiological environments even for individual's lifetime without showing any clinical symptoms of disease. However, in 10% of the cases these latent bacilli may reactivate to cause disease. One of the hypothesis about development of these persistent bacteria is pathophysiological environment in human lesions namely, reduced oxygen tension, nutrient limitation, and acidic pH. These factors have been postulated to render these bacteria phenotypically tolerant to major anti-mycobacterial drugs.

In addition to the management of the TB epidemic, there is the emerging problem of resistance to first-line antibiotic agents. Some important examples include penicillin-resistant *Streptococcus pneumoniae*, vancomycin-resistant enterococci, methicillin-resistant *Staphylococcus aureus*, multi-resistant salmonellae.

The consequences of resistance to antibiotic agents are severe. Infections caused by resistant microbes fail to respond to treatment, resulting in prolonged illness and greater risk of death. Treatment failures also lead to longer periods of infectivity, which increase the numbers of infected people moving in the community and thus exposing the general population to the risk of contracting a resistant strain infection.

Hospitals are a critical component of the antimicrobial resistance problem worldwide. The combination of highly susceptible patients, intensive and prolonged antimicrobial use, and cross-infection has resulted in infections with highly resistant bacterial pathogens.

Self-medication with antimicrobials is another major factor contributing to resistance. Self-medicated antimicrobials may be unnecessary, are often inadequately dosed, or may not contain adequate amounts of active drug.

Patient compliance with recommended treatment is another major problem. Patients forget to take medication, interrupt their treatment when they begin to feel better, or may be unable to afford a full course, thereby creating an ideal environment for microbes to adapt rather than be killed.

Because of the emerging resistance to multiple antibiotics, physicians are confronted with infections for which there is no effective therapy. The morbidity, mortality, and financial costs of such infections impose an increasing burden for health care systems worldwide.

Therefore, there is a high need for new compounds to treat bacterial infections, especially mycobacterial infections including drug resistant and latent mycobacterial infections, and also other bacterial infections especially those caused by resistant bacterial strains.

Anti-infective compounds for treating tuberculosis have been disclosed in e.g. international patent application WO 2011/113606. Such a document is concerned with compounds that would prevent *M. tuberculosis* multiplication inside the host macrophage and relates to compounds with a bicyclic core, imidazopyridines, which are linked (e.g. via an amido moiety) to e.g. an optionally substituted benzyl group.

International patent application WO2014/015167 also discloses compounds that are disclosed as being of potential use in the treatment of tuberculosis. Such compounds disclosed herein have a bicycle (a 5,5-fused bicycle) as an essential element, which is substituted by a linker group (e.g. an amido group), which itself may be attached to another bicycle or aromatic group. Such compounds in this document do not contain a series of more than three rings.

Journal article *Nature Medicine*, 19, 1157-1160 (2013) by Pethe et al "Discovery of Q203, a potent clinical candidate for the treatment of tuberculosis" identifies a specific compound that was tested against *M. tuberculosis*. This compound Q203 is depicted below.

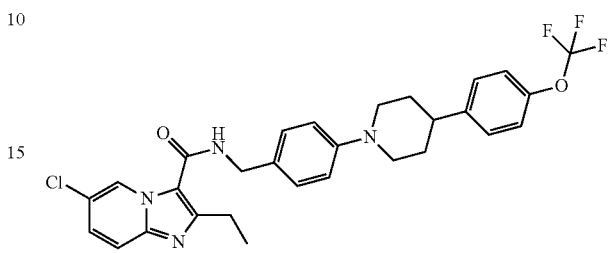

This clinical candidates is also discussed in journal article, *J. Medicinal Chemistry*, 2014, 57 (12), pp 5293-5305. It is stated to have activity against MDR tuberculosis, and have activity against the strain *M. tuberculosis* H37Rv at a $MIC_{50}$ of 0.28 nM inside macrophages. Positive control data (using known anti-TB compounds bedaquiline, isoniazid and moxifloxacin) are also reported. This document also suggests a mode of action, based on studies with mutants. It postulates that it acts by interfering with ATP synthase in *M. tuberculosis*, and that the inhibition of cytochrome $bc_1$ activity is the primary mode of action. Cytochrome $bc_1$ is an essential component of the electron transport chain required for ATP synthesis. It appeared that Q203 was highly active against both replicating and non-replicating bacteria International patent application WO 2015/014993 also discloses compounds as having activity against *M. tuberculosis*. International patent applications WO 2013/033070 and WO 2013/033167 disclose various compounds as kinase modulators.

The purpose of the present invention is to provide compounds for use in the treatment of bacterial diseases, particularly those diseases caused by pathogenic bacteria such as *Mycobacterium tuberculosis* (including the latent disease and including drug resistant *M. tuberculosis* strains). Such compounds may also be novel and may act by interfering with ATP synthase in *M. tuberculosis*, with the inhibition of cytochrome $bc_1$ activity being considered the primary mode of action.

SUMMARY OF THE INVENTION

There is now provided a compound of formula (I) for use in the treatment of tuberculosis

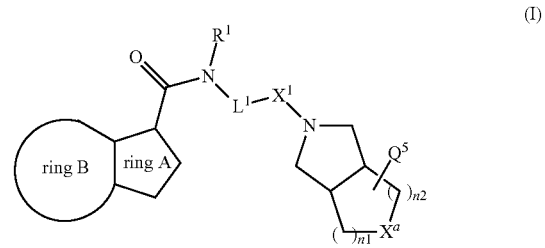

wherein

R$^1$ represents C$_{1-6}$ alkyl or hydrogen;

L$^1$ represents a linker group —C(R$^a$)(R$^b$)—;

X$^1$ represents an optional carbocyclic aromatic linker group (which linker group may itself be optionally substituted by one or more substituents selected from fluoro, —OH, —OC$_{1-6}$ alkyl and C$_{1-6}$ alkyl, wherein the latter two alkyl moieties are themseleves optionally substituted by one or more fluoro atoms);

n1 and n2 independently represent 0 or 1 (hence, the X$^a$-containing ring may be 3-, 4- or 5-membered, or (when m is 2), 6-membered);

R$^a$ and R$^b$ independently represent hydrogen or C$_{1-6}$ alkyl (optionally substituted by one or more fluoro atoms);

X$^a$ represents —C(R$^{a1}$)(R$^{b1}$)$_m$— or —N(R$^{c1}$)—;

m represents 1 or 2;

each R$^{a1}$ and R$^{b1}$ independently represents fluoro, hydrogen or C$_{1-6}$ alkyl;

R$^{c1}$ represents hydrogen or C$_{1-6}$ alkyl;

Q$^5$ represents one or more independent substituents selected from halo, C$_{1-6}$ alkyl, —OC$_{1-6}$ alkyl (which latter two alkyl moieties may themselves be optionally substituted by one or more halo, e.g. fluoro, atoms), aryl and heteroaryl (which latter two aromatic groups may themselves be optionally substituted by one or more substituents selected from halo, C$_{1-6}$ alkyl and —OC$_{1-6}$ alkyl, which latter two alkyl moieties may themselves be substituted with one or more fluoro atoms);

ring A is a 5-membered aromatic ring containing at least one heteroatom (preferably containing at least one nitrogen atom);

ring B is a 5- or 6-membered ring, which may be aromatic or non-aromatic, optionally containing one to four heteroatoms (preferably selected from nitrogen, oxygen and sulfur);

either ring A and/or ring B may be optionally substituted by one or more substituents selected from: halo, C$_{1-6}$ alkyl (optionally substituted by one or more halo, e.g. fluoro atoms) and/or —OC$_{1-6}$alkyl (itself optionally substituted by one or more fluoro atoms), or a pharmaceutically-acceptable salt thereof, which compounds may be referred to herein as "compounds of the invention".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

For the purposes of this invention solvates, prodrugs, N-oxides and stereoisomers of compounds of the invention are also included within the scope of the invention.

The term "prodrug" of a relevant compound of the invention includes any compound that, following oral or parenteral administration, is metabolised in vivo to form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration.

Prodrugs of compounds of the invention may be prepared by modifying functional groups present on the compound in such a way that the modifications are cleaved, in vivo when such prodrug is administered to a mammalian subject. The modifications typically are achieved by synthesising the parent compound with a prodrug substituent. Prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. 1-92, Elesevier, N.Y. -Oxford (1985).

Compounds of the invention may contain double bonds and may thus exist as E (entgegen) and Z (zusammen) geometric isomers about each individual double bond. Positional isomers may also be embraced by the compounds of the invention. All such isomers (e.g. if a compound of the invention incorporates a double bond or a fused ring, the cis- and trans-forms, are embraced) and mixtures thereof are included within the scope of the invention (e.g. single positional isomers and mixtures of positional isomers may be included within the scope of the invention).

Compounds of the invention may also exhibit tautomerism. All tautomeric forms (or tautomers) and mixtures thereof are included within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganisation of some of the bonding electrons.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person.

All stereoisomers (including but not limited to diastereoisomers, enantiomers and atropisomers) and mixtures thereof (e.g. racemic mixtures) are included within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{123}I$, and $^{125}I$. Certain isotopically-labeled compounds of the present invention (e.g., those labeled with $^{3}H$ and $^{14}C$) are useful in compound and for substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$ may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Scheme 1 and/or in the Examples herein below, by substituting an isotopically labeled reagent for a non-isotopically labeled reagent.

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). Such cycloalkyl groups may be monocyclic or bicyclic and may further be bridged. Further, when there is a sufficient number (i.e. a minimum of four) of carbon atoms, such groups may also be part cyclic. Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group).

$C_{3-q}$ cycloalkyl groups (where q is the upper limit of the range) that may be specifically mentioned may be monocyclic or bicyclic alkyl groups, which cycloalkyl groups may further be bridged (so forming, for example, fused ring systems such as three fused cycloalkyl groups). Such cycloalkyl groups may be saturated or unsaturated containing one or more double bonds (forming for example a cycloalkenyl group). Substituents may be attached at any point on the cycloalkyl group. Further, where there is a sufficient number (i.e. a minimum of four) such cycloalkyl groups may also be part cyclic.

The term "halo", when used herein, preferably includes fluoro, chloro, bromo and iodo.

Heterocyclic groups when referred to herein may include aromatic or non-aromatic heterocyclic groups, and hence encompass heterocycloalkyl and hetereoaryl. Equally, "aromatic or non-aromatic 5- or 6-membered rings" may be heterocyclic groups (as well as carbocyclic groups) that have 5- or 6-members in the ring.

Heterocycloalkyl groups that may be mentioned include non-aromatic monocyclic and bicyclic heterocycloalkyl groups in which at least one (e.g. one to four) of the atoms in the ring system is other than carbon (i.e. a heteroatom), and in which the total number of atoms in the ring system is between 3 and 20 (e.g. between three and ten, e.g. between 3 and 8, such as 5- to 8-). Such heterocycloalkyl groups may also be bridged. Further, such heterocycloalkyl groups may be saturated or unsaturated containing one or more double and/or triple bonds, forming for example a $C_{2-q}$ heterocloalkenyl (where q is the upper limit of the range) group. $C_{2-q}$ heterocycloalkyl groups that may be mentioned include 7-azabicyclo[2.2.1]heptanyl, 6-azabicyclo[3.1.1]heptanyl, 6-azabicyclo[3.2.1]-octanyl, 8-azabicyclo-[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo-[3.2.1]octanyl, oxetanyl, oxiranyl, piperazinyl, piperidinyl, non-aromatic pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form. Heterocycloalkyl mentioned herein may be stated to be specifically monocyclic or bicyclic.

Aryl groups that may be mentioned include $C_{6-20}$, such as $C_{6-12}$ (e.g. $C_{6-10}$) aryl groups. Such groups may be monocyclic, bicyclic or tricyclic and have between 6 and 12 (e.g. 6 and 10) ring carbon atoms, in which at least one ring is aromatic. $C_{6-10}$ aryl groups include phenyl, naphthyl and the like, such as 1,2,3,4-tetrahydronaphthyl. The point of attachment of aryl groups may be via any atom of the ring system. For example, when the aryl group is polycyclic the point of attachment may be via atom including an atom of a non-aromatic ring. However, when aryl groups are polycyclic (e.g. bicyclic or tricyclic), they are preferably linked to the rest of the molecule via an aromatic ring. Most preferred aryl groups that may be mentioned herein are "phenyl".

Unless otherwise specified, the term "heteroaryl" when used herein refers to an aromatic group containing one or more heteroatom(s) (e.g. one to four heteroatoms) preferably selected from N, O and S. Heteroaryl groups include those which have between 5 and 20 members (e.g. between 5 and 10) and may be monocyclic, bicyclic or tricyclic, provided that at least one of the rings is aromatic (so forming, for example, a mono-, bi-, or tricyclic heteroaromatic group). When the heteroaryl group is polycyclic the point of attachment may be via any atom including an atom of a non-aromatic ring. However, when heteroaryl groups are polycyclic (e.g. bicyclic or tricyclic), they are preferably linked to the rest of the molecule via an aromatic ring. Heteroaryl groups that may be mentioned include 3,4-dihydro-1H-isoquinolinyl, 1,3-dihydroisoindolyl, 1,3-dihydroisoindolyl (e.g. 3,4-dihydro-1H-isoquinolin-2-yl, 1,3-dihydroisoindol-2-yl, 1,3-dihydroisoindol-2-yl; i.e. heteroaryl groups that are linked via a non-aromatic ring), or, preferably, acridinyl, benzimidazolyl, benzodioxanyl, benzodioxepinyl, benzodioxolyl (including 1,3-benzodioxolyl), benzofuranyl, benzofurazanyl, benzothiadiazolyl (including 2,1,3-benzothiadiazolyl), benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazolyl, isothiochromanyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N- or S-oxidised form. Heteroaryl groups mentioned herein may be stated to be specifically monocyclic or bicyclic. When heteroaryl groups are polycyclic in which there is a non-aromatic ring present, then that non-aromatic ring may be substituted by one or more =O group. Most preferred heteroaryl groups that may be mentioned herein are 5- or 6-membered aromatic groups containing 1, 2 or 3 heteroatoms (e.g. preferably selected from nitrogen, oxygen and sulfur).

It may be specifically stated that the heteroaryl group is monocyclic or bicyclic. In the case where it is specified that the heteroaryl is bicyclic, then it may consist of a five-, six- or seven-membered monocyclic ring (e.g. a monocyclic heteroaryl ring) fused with another five-, six- or seven-membered ring (e.g. a monocyclic aryl or heteroaryl ring).

Heteroatoms that may be mentioned include phosphorus, silicon, boron and, preferably, oxygen, nitrogen and sulfur.

When "aromatic" groups are referred to herein, they may be aryl or heteroaryl. When "aromatic linker groups" are referred to herein, they may be aryl or heteroaryl, as defined herein, are preferably monocyclic (but may be polycyclic) and attached to the remainder of the molecule via any possible atoms of that linker group. However, when, specifically carbocyclic aromatic linker groups are referred to, then such aromatic groups may not contain a heteroatom, i.e. they may be aryl (but not heteroaryl).

For the avoidance of doubt, where it is stated herein that a group may be substituted by one or more substituents (e.g. selected from $C_{1-6}$ alkyl), then those substituents (e.g. alkyl groups) are independent of one another. That is, such groups may be substituted with the same substituent (e.g. same alkyl substituent) or different (e.g. alkyl) substituents.

For the avoidance of doubt, there has to be at least one $Q^5$ substituent present, and where $Q^5$ is mentioned herein, this represents one or more substituents on the bicycle to which it is attached, and such substituents may be situated on either (or both) rings of such bicycle (i.e. the N-containing 5-membered ring and/or the $X^a$-containing ring).

All individual features (e.g. preferred features) mentioned herein may be taken in isolation or in combination with any other feature (including preferred feature) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

Certain (e.g. preferred) aspects of compounds of the invention include those in which:
$R^1$ represents hydrogen;
$R^a$ and $R^b$ independently represent hydrogen;
$L^1$ represents —$CH_2$—;
when $X^1$ is present, then it represents a carbocyclic aromatic linker group, for example a phenyl group or a bicyclic (carbocyclic) aromatic linker group (in which at least one of the rings of the bicycle is aromatic), for instance such that the bicycle consists of two separate rings fused with each other, in which each ring is 5- or 6-membered so forming a 6,6-, 5,6- or 5,5-fused bicyclic ring), hence including groups such as phenyl, naphthyl (including fully aromatic naphthyl and 1,2,3,4-tetrahydronaphthyl) and the like, so forming e.g. in particular:
phenylene—(especially a 1,4-phenylene), e.g.:

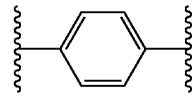

naphthylene, e.g.:

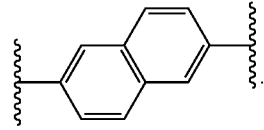

Such linker groups that $X^1$ may represent (e.g. phenylene) may be optionally substituted (e.g. by one or more substituents selected from fluoro, $CH_3$, $CF_3$, —$OCH_3$ and —$OCF_3$). In an embodiment such linker groups that $X^1$ may represent are unsubstituted.

Further aspects of the invention (or further aspects of compounds of the invention) that may be mentioned include those in which:
$X^a$ represents —$CH_2$— which is substituted (e.g. at the $X^a$ position) by one or more (e.g. one or two) $Q^5$ substituent(s);

$Q^5$ represents halo (e.g. fluoro) or $C_{1-3}$ alkyl (optionally substituted by one or more fluoro atoms).

In a yet further aspect of the invention, there is provided compounds of the invention in which:

one or two $Q^5$ substituents are present on the fused bicycle containing $X^a$;

(one or two) $Q^5$ substituents is/are only present on $X^a$ (and not on other atoms of that fused bicycle).

In two different aspects of the invention:

n1 and n2 both represent 1;
n1 and n2 both represent 0.

It is preferred that compounds of the invention comprise:

ring A, which is an aromatic ring containing at least one to three (e.g. one or two) heteroatoms, preferably contains at least one nitrogen atom;

ring B is more preferably also an aromatic ring (e.g. a 5- or especially a 6-membered aromatic ring), preferably containing at least one nitrogen atom.

It is preferred that Ring A of the compounds of the invention are represented as follows:

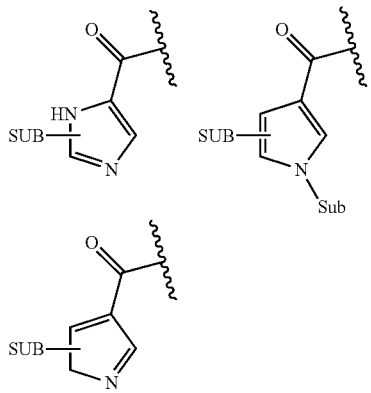

Other preferred ring A moieties include:

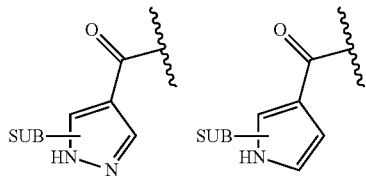

Monocyclic heteroaryl groups that may be mentioned include 5- or 6-membered rings containing one to four heteroatoms (preferably selected from nitrogen, oxygen and sulfur). It is preferred that Ring B of the compounds of the invention are represented as follows:

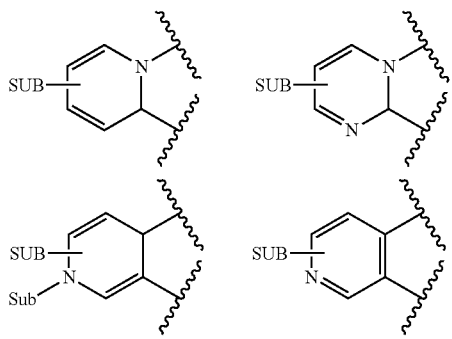

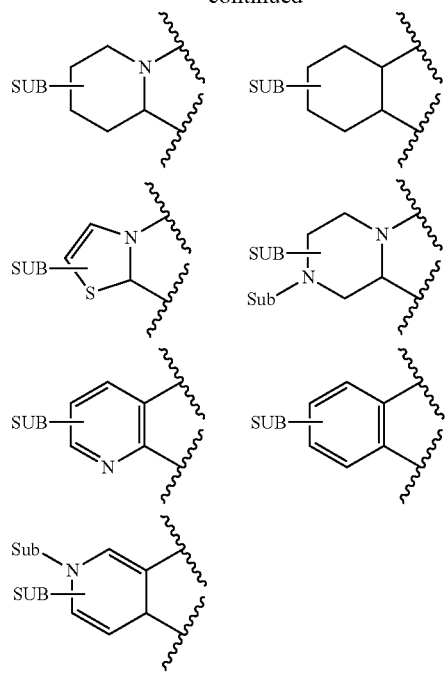

where "SUB" may be a relevant optional substituent (or more than when relevant substituent, where possible) on a carbon atom or, where possible, on a heteroatom e.g. on a NH, thus replacing the H.

Other preferred "Ring B" moieties include:

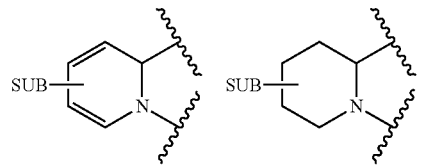

Preferred substituents (when present; e.g such optional substituents may be absent or there may be one) on ring B include $C_{1-3}$ alkyl (e.g. methyl) or halo (e.g. bromo or, more preferably, chloro). Other preferred substituents on ring B include —$OC_{1-6}$alkyl (e.g. —$OC_{1-3}$alkyl, such as —$OCH_3$).

Preferred substituents (when present; e.g such optional substituents may be absent or there may be one) on ring B include $C_{1-3}$ alkyl (e.g. methyl) or halo (e.g. bromo or, more preferably, chloro). Preferred substituents (when present; preferably, there may be one or two substituents) on ring A include $C_{1-3}$ alkyl (e.g. methyl or ethyl). When $L^2$ represents an aromatic group (e.g. phenyl or pyridyl) and such groups are substituted, preferred substituents include halo and especially —$OC_{1-3}$ alkyl (e.g. —O-methyl), where the latter is substituted by fluoro, so forming for example a —$OCF_3$ group.

The combined ring systems, i.e. Ring A and Ring B may be represented as follows:

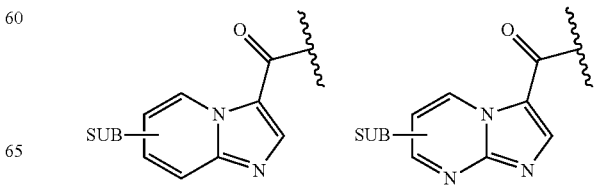

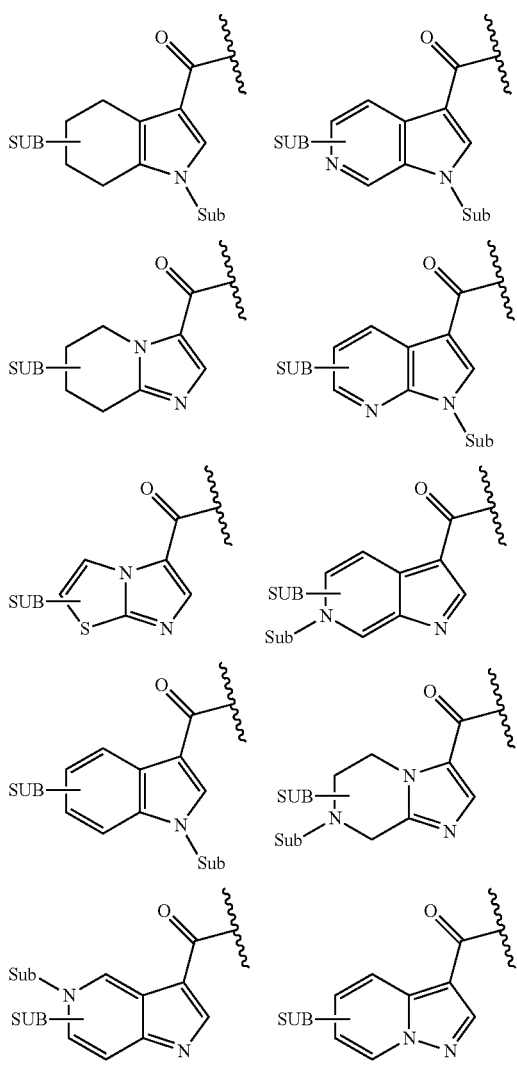

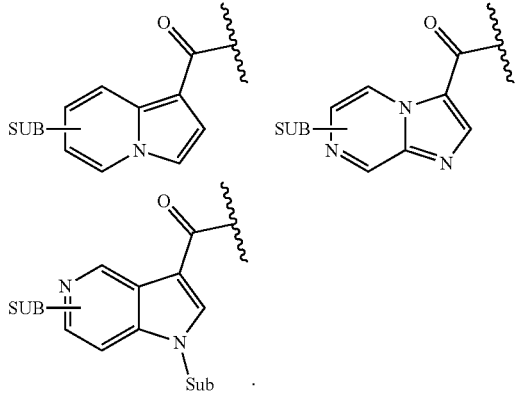

where "SUB" represents one or more possible substituents on the bicycle (i.e. on ring A and/or on ring B) and "Sub" represents a possible optional substituent on the N atom of the bicycle (unsubstituted in this context would mean "NH").

Other combined ring A and ring B systems that may be mentioned include the following:

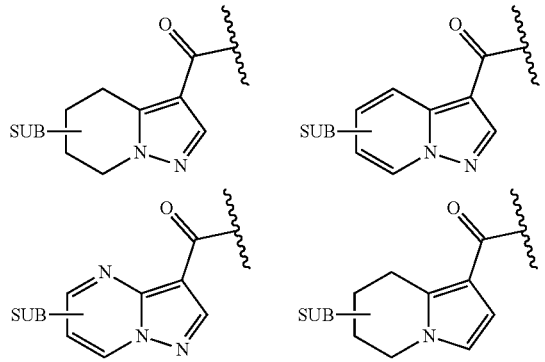

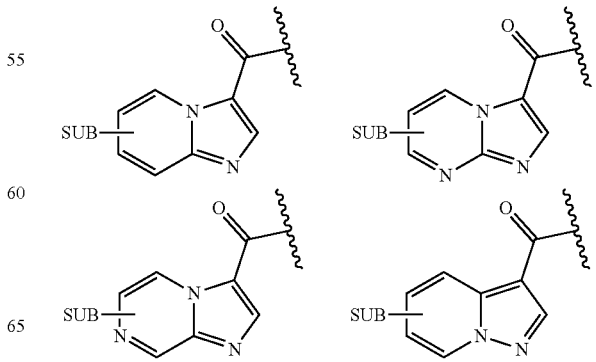

Certain compounds of the invention are mentioned (e.g. hereinbefore) for use in the treatment of tuberculosis. Certain of such compounds mentioned herein may also be novel per se. And certain of such compounds mentioned herein may be novel as medicaments/pharmaceuticals (or novel as a component of a pharmaceutical composition/formulation). Hence, in further aspects of the invention, there is provided the following compounds per se or following compounds for use as pharmaceuticals/medicaments (in the latter case such compounds may be components of a pharmaceutical composition/formulation):

(I) Compounds of formula (I) as hereinbefore defined and in which:
  $L^1$ represents —CH$_2$—;
  $X^a$ represents —CH$_2$— and which is substituted (e.g. at the $X^a$ position) by one or two $Q^5$ substituent(s);

(II) Compounds of formula (I) as hereinbefore defined (e.g. at (I) above) and in which: $Q^5$ represents halo (e.g. fluoro) or $C_{1-3}$ alkyl (optionally substituted by one or more fluoro atoms);
  (one or two) $Q^5$ substituents is/are only present on $X^a$ (and not on other atoms of that fused bicycle);
  ring A and ring B together represent a 8 or 9-membered bicyclic ring (ring A is a 5-membered ring and ring B may be a 5 or 6-membered ring, in which both rings are preferably aromatic) containing at least one nitrogen atom (and in a major embodiment, at least one nitrogen atom that is common to both rings); optional substituents on ring A and ring B are halo, $C_{1-3}$ alkyl and —OC$_{1-3}$ alkyl; and
  other integers are as defined herein; and/or (III) Compounds as hereinbefore defined (e.g. at (I) and/or (II) above) and further in which the ring A and ring B bicycles are represented as defined herein or more particulary as follows:

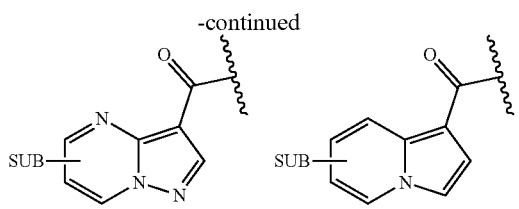

(or any one of the above-mentioned representations).

Pharmacology

The compounds according to the invention have surprisingly been shown to be suitable for the treatment of a bacterial infection including a mycobacterial infection, particularly those diseases caused by pathogenic mycobacteria such as *Mycobacterium tuberculosis* (including the latent and drug resistant form thereof). The present invention thus also relates to compounds of the invention as defined hereinabove, for use as a medicine, in particular for use as a medicine for the treatment of a bacterial infection including a mycobacterial infection.

Such compounds of the invention may act by interfering with ATP synthase in *M. tuberculosis*, with the inhibition of cytochrome $bc_1$ activity being the primary mode of action. Cytochrome $bc_1$ is an essential component of the electron transport chain required for ATP synthesis.

Further, the present invention also relates to the use of a compound of the invention, as well as any of the pharmaceutical compositions thereof as described hereinafter for the manufacture of a medicament for the treatment of a bacterial infection including a mycobacterial infection.

Accordingly, in another aspect, the invention provides a method of treating a patient suffering from, or at risk of, a bacterial infection, including a mycobacterial infection, which comprises administering to the patient a therapeutically effective amount of a compound or pharmaceutical composition according to the invention.

The compounds of the present invention also show activity against resistant bacterial strains.

Whenever used hereinbefore or hereinafter, that the compounds can treat a bacterial infection it is meant that the compounds can treat an infection with one or more bacterial strains.

The invention also relates to a composition comprising a pharmaceutically acceptable carrier and, as active ingredient, a therapeutically effective amount of a compound according to the invention. The compounds according to the invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions, or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight, even more preferably from 0.1 to 50% by weight of the active ingredient(s), and, from 1 to 99.95% by weight, more preferably from 30 to 99.9% by weight, even more preferably from 50 to 99.9% by weight of a pharmaceutically acceptable carrier, all percentages being based on the total weight of the composition.

The pharmaceutical composition may additionally contain various other ingredients known in the art, for example, a lubricant, stabilising agent, buffering agent, emulsifying agent, viscosity-regulating agent, surfactant, preservative, flavouring or colorant.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The daily dosage of the compound according to the invention will, of course, vary with the compound employed, the mode of administration, the treatment desired and the mycobacterial disease indicated. However, in general, satisfactory results will be obtained when the compound according to the invention is administered at a daily dosage not exceeding 1 gram, e.g. in the range from 10 to 50 mg/kg body weight.

Given the fact that the compounds of formula (Ia) or Formula (Ib) are active against bacterial infections, the present compounds may be combined with other antibacterial agents in order to effectively combat bacterial infections.

Therefore, the present invention also relates to a combination of (a) a compound according to the invention, and (b) one or more other antibacterial agents.

The present invention also relates to a combination of (a) a compound according to the invention, and (b) one or more other antibacterial agents, for use as a medicine.

The present invention also relates to the use of a combination or pharmaceutical composition as defined directly above for the treatment of a bacterial infection.

A pharmaceutical composition comprising a pharmaceutically acceptable carrier and, as active ingredient, a therapeutically effective amount of (a) a compound according to the invention, and (b) one or more other antibacterial agents, is also comprised by the present invention.

The weight ratio of (a) the compound according to the invention and (b) the other antibacterial agent(s) when given as a combination may be determined by the person skilled in the art. Said ratio and the exact dosage and frequency of administration depends on the particular compound according to the invention and the other antibacterial agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of the invention and another antibacterial agent may range from 1/10 to 10/1, more in particular from 1/5 to 5/1, even more in particular from 1/3 to 3/1.

The compounds according to the invention and the one or more other antibacterial agents may be combined in a single preparation or they may be formulated in separate preparations so that they can be administered simultaneously, separately or sequentially. Thus, the present invention also relates to a product containing (a) a compound according to the invention, and (b) one or more other antibacterial agents, as a combined preparation for simultaneous, separate or sequential use in the treatment of a bacterial infection.

The other antibacterial agents which may be combined with the compounds of the invention are for example antibacterial agents known in the art. For example, the compounds of the invention may be combined with antibacterial agents known to interfere with the respiratory chain of *Mycobacterium tuberculosis*, including for example direct inhibitors of the ATP synthase (e.g. bedaquiline, bedaquiline fumarate or any other compounds that may have be disclosed in the prior art, e.g. compounds disclosed in WO2004/011436), inhibitors of ndh2 (e.g. clofazimine) and inhibitors of cytochrome bd. Additional mycobacterial agents which may be combined with the compounds of the invention are for example rifampicin (=rifampin); isoniazid; pyrazinamide; amikacin; ethionamide; ethambutol; streptomycin; para-aminosalicylic acid; cycloserine; capreomycin; kanamycin; thioacetazone; PA-824; delamanid; quinolones/fluoroquinolones such as for example moxifloxacin, gatifloxacin, ofloxacin, ciprofloxacin, sparfloxacin; macrolides such as for example clarithromycin, amoxycillin with clavulanic acid; rifamycins; rifabutin; rifapentin; as well as others, which are currently being developed (but may not yet be on the market; see e.g. http://www.newtbdrugs.org/pipeline.php).

General Preparation

The compounds according to the invention can generally be prepared by a succession of steps, each of which may be known to the skilled person or described herein.

EXPERIMENTAL PART

Compounds of formula I may be prepared in accordance with the techniques employed in the examples hereinafter (and those methods know by those skilled in the art), for example by using the following techniques.

Compounds of formula (I) may be prepared by:
(i) reaction of a compound of formula (II),

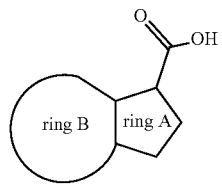

(II)

wherein the integers are as hereinbefore defined, or a suitable derivative thereof, such as a carboxylic acid ester derivative, with a compound of formula (III)

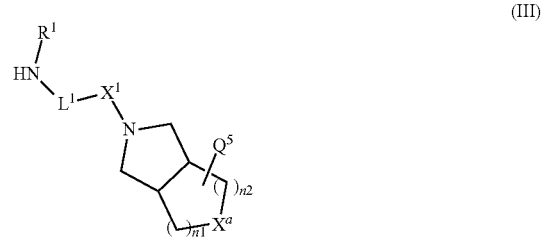

(III)

wherein the integers are as hereinbefore defined, under amide coupling reaction conditions, for example in the presence of a suitable coupling reagent (e.g. 1,1'-carbonyldiimidazole, N,N'-dicyclohexylcarbodiimide, 1-(3-dimethylaminopropyl)-3-ethylcarbodiimide (or hydrochloride thereof) or N,N'-disuccinimidyl carbonate), optionally in the presence of a suitable base (e.g. sodium hydride, sodium bicarbonate, potassium carbonate, pyridine, triethylamine, dimethylaminopyridine, diisopropylamine, sodium hydroxide, potassium tert-butoxide and/or lithium diisopropylamide (or variants thereof) and an appropriate solvent (e.g. tetrahydrofuran, pyridine, toluene, dichloromethane, chloroform, acetonitrile, dimethylformamide, trifluoromethylbenzene, dioxane or triethylamine). Alternatively, the carboxylic acid group of the compound of formula (IV) may first be converted under standard conditions to the corresponding acyl chloride (e.g. in the presence of $POCl_3$, $PCl_5$, $SOCl_2$ or oxalyl chloride), which acyl chloride is then reacted with a compound of formula (V), for example under similar conditions to those mentioned above;

(ii) coupling of a compound of formula (IV),

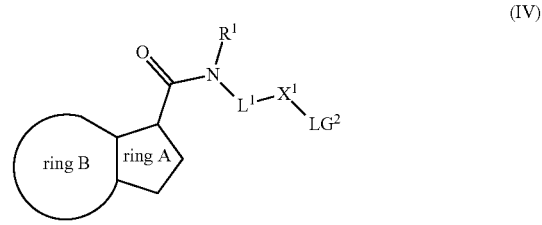

(IV)

wherein the integers are as hereinbefore defined, and $LG^2$ represents a suitable leaving group, such as iodo, bromo, chloro or a sulfonate group (for example a type of group that may be deployed for a coupling), with a compound of formula (V),

(V)

wherein the integers are as hereinbefore defined, under standard conditions, for example optionally in the presence of an appropriate metal catalyst (or a salt or complex thereof) such as $Pd(dba)_2$, $Pd(OAc)_2$, Cu, $Cu(OAc)_2$, Cu, $NiCl_2$ or the like, with an optional additive such as $Ph_3P$, X-phos or the like, in the presence of an appropriate base (e.g. t-BuONa, or the like) in a suitable solvent (e.g. dioxane or the like) under reaction conditions known to those skilled in the art.

Other steps that may be mentioned include:
nucleophilic aromatic substitution reactions
other coupling reactions e.g. in which one compound contains a suitable leaving group such as one described hereinbefore with respect to $LG^2$ (and may particularly represent chloro, bromo or iodo), with another compound comprising a mutually compatible "leaving group" or another suitable group such as —B(OH)$_2$, —B(OR$^{wx}$)$_2$ or —SN(R$^{wx}$)$_3$, in which each R$^{wx}$ independently represents a $C_{1-6}$ alkyl group, or, in the case of —B(OR$^{wx}$)$_2$, the respective R$^{wx}$ groups may be linked together to form a 4- to 6-membered cyclic group, thereby forming e.g. a pinacolato boronate ester group (or may represent iodo, bromo or chloro, provided that the "leaving groups" are mutually compatible), and wherein the reaction may be performed in the presence of a suitable catalyst system, e.g. a metal (or a salt or complex thereof) such as Pd, CuI, Pd/C, PdCl$_2$, Pd(OAc)$_2$, Pd(Ph$_3$P)$_2$Cl$_2$, Pd(Ph$_3$P)$_4$, Pd$_2$(dba)$_3$ and/or NiCl$_2$ (or the like) and a ligand such as PdCl$_2$(dppf). DCM, t-Bu$_3$P, (C$_6$H$_{11}$)$_3$P, Ph$_3$P or the like, in a suitable solvent and under reaction conditions known to those skilled in the art.

It is evident that in the foregoing and in the following reactions, the reaction products may be isolated from the reaction medium and, if necessary, further purified according to methodologies generally known in the art, such as extraction, crystallization and chromatography. It is further evident that reaction products that exist in more than one enantiomeric form, may be isolated from their mixture by known techniques, in particular preparative chromatography, such as preparative HPLC, chiral chromatography. Individual diastereoisomers or individual enantiomers can also be obtained by Supercritical Fluid Chromatography (SCF).

The starting materials and the intermediates are compounds that are either commercially available or may be prepared according to conventional reaction procedures generally known in the art.

EXAMPLES

Synthesis of Compound 1

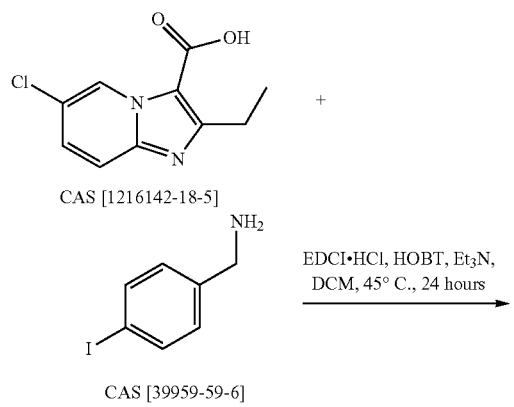

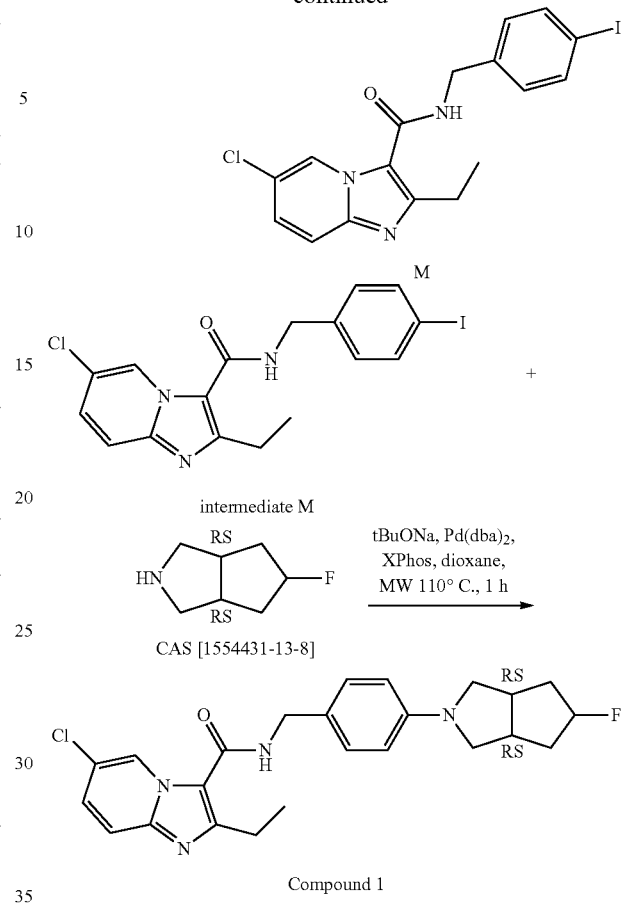

Preparation of Intermediate M

A solution of 6-chloro-2-ethylimidazo[3,2-a]pyridine-3-carboxylic acid (CAS [12161242-18-5], 1 g, 4.45 mmol), 4-iodobenzenemethanamine (CAS [39959-59-6], 1.09 g, 4.67 mmol), EDCI.HCl (1.28 g, 6.68 mmol), HOBT (0.601 g, 4.45 mmol) and triethylamine (1.24 mL, 9 mmol) in dichloromethane (8 mL) was stirred and heated at 45° C. for 24 hours. The solution was cooled down to 15° C. The solid was collected by filtration, washed with water and acetonitrile and the solid was dried (vacuum, 45° C., 1 hour) to give intermediate M, 1.2 g, 55%.

Preparation of Compound 1

A solution of 5-fluorooctahydrocyclopenta[c]pyrrole (CAS [1554431-13-8], 0.1 g, 0.604 mmol), intermediate M (0.319 g, 0.725 mmol), Pd(dba)$_2$ (0.035 g, 0.06 mmol), Xphos (0.052 g, 0.12 mmol) and sodium tert-butoxide (0.29 g, 3.02 mmol) in 1,4-dioxane (5 mL) was irradiated under microwave at 110° C. for 1 h under N2. Dichloromethane (50 mL) was added and the mixture was washed with water (50 mL) and brine (50 mL). The organic layer was dried over sodium sulfate, filtered and the filtrate was concentrated under vacuum. The residue was purified by column chromatography over silica gel (eluent: petroleum ether/ethyl acetate 1/0 to 0/1). The desired fractions were collected and concentrated. The residue was washed with methanol (10 mL), dried (vacuum, 45° C., 1 hour) to give Compound 1, 0.105 g, 38%.

$^1$H NMR (400 MHz, CHLOROFORM-d) δ=9.52 (d, J=1.7 Hz, 1H), 7.70 (d, J=8.1 Hz, 1H), 7.58-7.48 (m, 1H), 7.34-7.27 (m, 1H), 7.24 (d, J=8.6 Hz, 2H), 7.13 (d, J=8.1 Hz, 1H), 6.67-6.56 (m, 2H), 6.14 (br. s., 1H), 5.99 (br. s., 1H), 5.35-5.12 (m, 1H), 4.64 (d, J=5.9 Hz, 1H), 4.58 (d, J=5.4 Hz, 2H), 3.39-3.28 (m, 2H), 3.20 (dd, J=2.2, 9.5 Hz, 2H), 2.99-2.98 (m, 1H), 3.08-2.98 (m, 2H), 2.94 (q, J=7.5 Hz, 2H), 2.43-2.23 (m, 2H), 1.82-1.72 (m, 1H), 1.66-1.62 (m, 1H), 1.43-1.32 (m, 3H)

Synthesis of Compound 2, Compound 3 and Compound 4

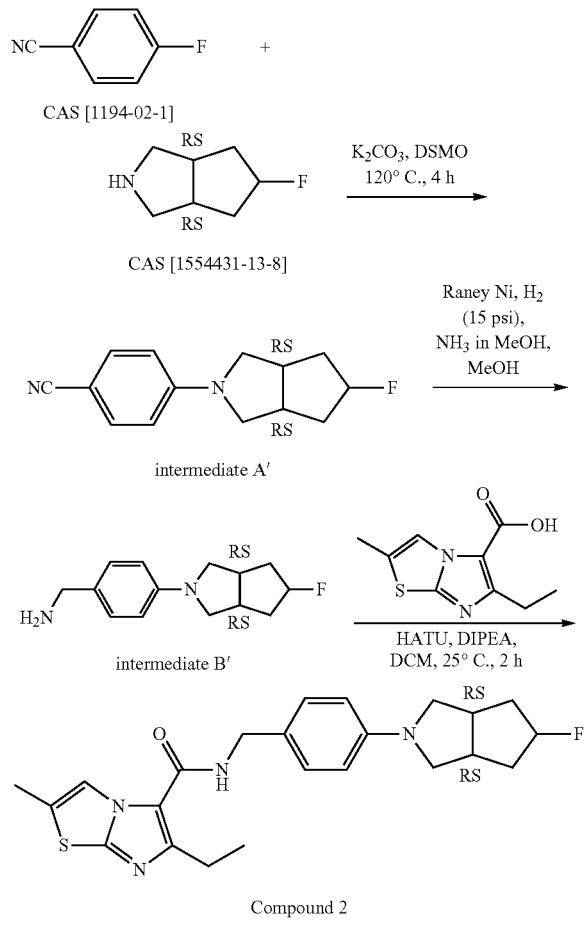

Preparation of Intermediate A'

A mixture of 4-fluorobenzonitrile (CAS [1194-02-1], 0.366 g, 3.02 mmol), 5-fluorooctahydrocyclopenta[c]pyrrole (CAS [1554431-13-8], 0.5 g, 3.02 mmol) and potassium carbonate (1.25 g, 9.06 mmol) in DMSO (50 mL) was stirred at 120° C. for 4 hours. The mixture was diluted with ethyl acetate (10 mL) and the mixture was washed with water (50 mL) and brine (50 mL). The separated organic layer was dried over magnesium sulfate, filtered and concentrated under vacuum. The residue was purified by column chromatography over silica gel (eluent: petroleum ether/ethyl acetate 10/1) to give intermediate A', 0.43 g, 590/%.

Preparation of Intermediate B'

A solution of intermediate A' (0.38 g, 1.65 mmol) in ammonia 7M in MeOH (7 M, 20 mL) was hydrogenated (15 psi) at 15° C. with Raney Nickel (0.038 g) as a catalyst for 16 hours. The catalyst was filtered off and the filtrate was concentrated under vacuum to give intermediate B', 0.38 g, 98%.

Preparation of Compound 2

A mixture of 6-Ethyl-2-imidazo[2,1b]thiazole-5-carboxylic acid (CAS [1131613-58-5], 0.09 g, 0.427 mmol), intermediate B' (0.1 g, 0.427 mmol), HATU (0.211 g, 0.555 mmol) and DIPEA (0.166 g, 1.28 mmol) in dichloromethane (2 mL) was stirred at 25° C. for 2 hours. The mixture was purified by high performance liquid chromatography over Gemini 150×25×5μ (eluent: 0.05% ammonium water/acetonitrile 21/79). The desired fractions were collected and lyophilized to give crude product. The crude product was further purified by high performance liquid chromatography over Boston Green ODS 150×30×5μ (eluent: 0.05% hydrochloride water/acetonitrile 40/60 to 30/70). The desired fractions were collected and lyophilized to give pure Compound 2 as HCl salt, 0.05 g, 24% $^1$H NMR (400 MHz, DMSO-d6) δ ppm 8.89 (t, J=5.8 Hz, 1H), 8.15 (d, J=1.5 Hz, 1H), 7.37 (d, J=8.3 Hz, 2H), 7.29 (br. s., 2H), 5.37-5.14 (m, 1H), 4.45 (d, J=5.8 Hz, 2H), 3.53 (br. s., 2H), 3.37 (d, J=9.8 Hz, 2H), 3.03 (q, J=7.4 Hz, 4H), 2.50 (s, 3H), 2.25-2.08 (m, 2H), 2.06-1.78 (m, 2H), 1.27 (t, J=7.5 Hz, 3H)

Preparation of Compound 3

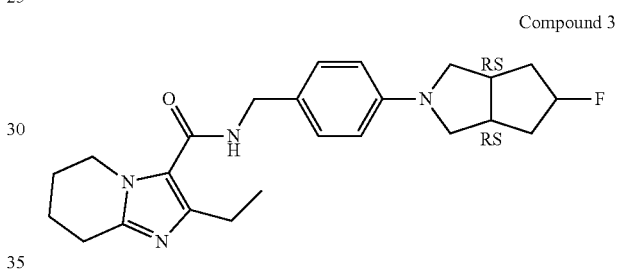

Compound 3

Accordingly, Compound 3 was prepared in the same way as Compound 2, starting from 2-ethyl-5H,6H,7H, 8H-imidazo[1,2-a]pyridine-3-carboxylic acid CAS [1529528-99-1] and intermediate B', yielding 0.045 g, 28%.

$^1$H NMR (400 MHz, CHLOROFORM-d) δ ppm 7.20 (d, J=8.4 Hz, 2H), 6.61 (d, J=8.4 Hz, 2H), 5.84 (br. s., 1H), 5.36-5.10 (m, 1H), 4.48 (d, J=5.3 Hz, 2H), 4.22 (t, J=5.7 Hz, 2H), 3.40-3.26 (m, 2H), 3.25-3.12 (m, 2H), 3.09-2.96 (m, 2H), 2.85 (t, J=6.2 Hz, 2H), 2.67 (q, J=7.5 Hz, 2H), 2.42-2.21 (m, 2H), 1.98-1.83 (m, 4H), 1.81-1.57 (m, 2H), 1.23 (t, J=7.5 Hz, 3H)

Preparation of Compound 4

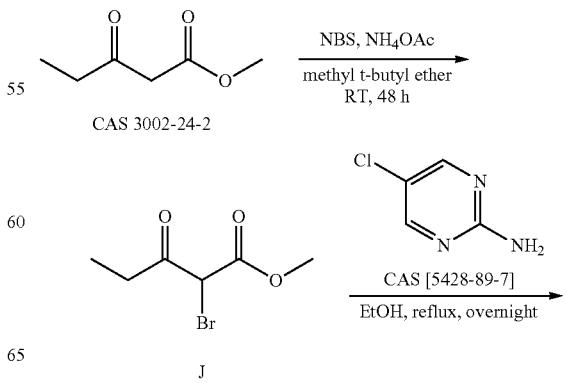

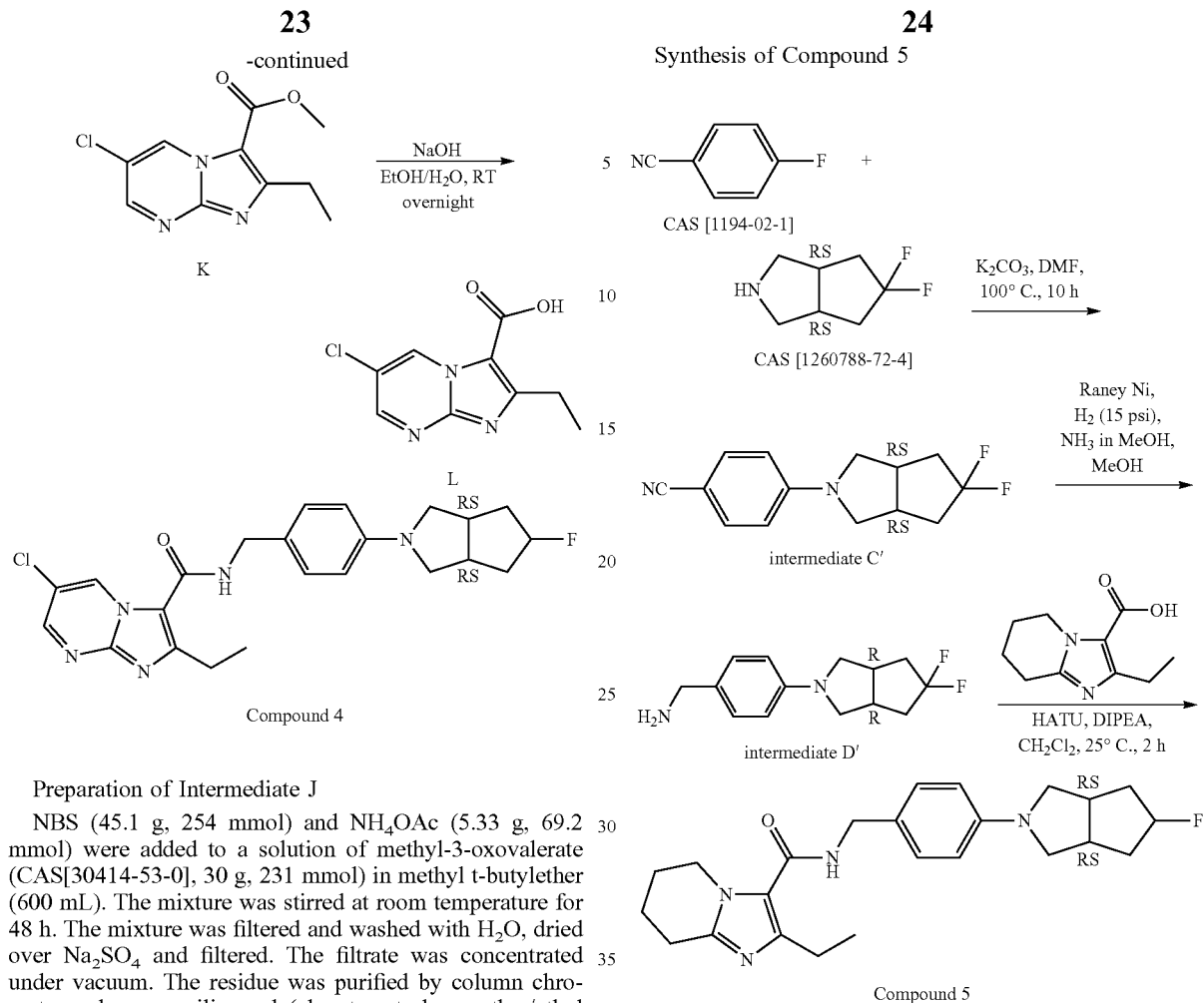

Synthesis of Compound 5

Preparation of Intermediate J

NBS (45.1 g, 254 mmol) and NH$_4$OAc (5.33 g, 69.2 mmol) were added to a solution of methyl-3-oxovalerate (CAS[30414-53-0], 30 g, 231 mmol) in methyl t-butylether (600 mL). The mixture was stirred at room temperature for 48 h. The mixture was filtered and washed with H$_2$O, dried over Na$_2$SO$_4$ and filtered. The filtrate was concentrated under vacuum. The residue was purified by column chromatography over silica gel (eluent: petroleum ether/ethyl acetate 20/1) to give intermediate J (20.0 g, yield: 35%).

Preparation of Intermediate K

A solution of 5-Chloro-2-pyridinamine (CAS [5428-89-7], 12.0 g, 93.0 mmol) and intermediate J (25.0 g, 112 mmol) in ethanol (60 mL) was refluxed overnight. The mixture was concentrated under vacuum. The residue was dissolved into ethyl acetate (100 mL). The solution was washed with water (2×100 mL), brine (100 mL), dried over sodium sulfate, filtered and concentrated under vacuum. The residue was purified by column chromatography over silica gel (eluent: petroleum ether/ethyl acetate 3/1) to give intermediate K (700 mg, yield: 3%).

Preparation of Intermediate L

A mixture of intermediate K (700 mg, 2.10 mmol) and sodium hydroxide (252 mg, 6.30 mmol) in ethanol (2 ml) and H$_2$O (2 mL) was stirred overnight at room temperature. Water (20 mL) was added and the solution was acidified with 2 M aqueous hydrochloride to pH ~3. The solution was lyophilized to give crude intermediate L (2 g).

Preparation of Compound 4

Accordingly, Compound 4 was prepared in the same way as Compound 2, starting from intermediate L and intermediate B', yielding 0.031 g, 16%.

$^1$H NMR (400 MHz, CHLOROFORM-d) δ ppm 9.52 (s, 1H), 8.5 (s, 1H), 7.2 (d, J=8.4 Hz, 2H), 6.54 (d, J=9.3 Hz, 2H), 6.02 (br. s., 1H), 5.99 (br. s., 1H), 4.58 (s, 2H), 3.32 (m, 2H), 3.28 (m, 2H), 2.94 (m, 4H), 2.3-2.4 (m, 2H), 1.6-1.7 (m, 2H), 1.38 (t, J=7.3 Hz, 3H)

Preparation of Intermediate C'

To a solution of 5,5-difluorooctahydrocyclopenta[c]pyrrole (CAS [1260788-72-4], 0.3 g, 2.04 mmol) in DMF (20 mL) was added 4-fluorobenzonitrile (CAS [1194-02-1], 0.245 g, 2.04 mmol) and potassium carbonate (0.563 g, 4.08 mmol). The mixture was stirred at 100° C. for 10 h. The mixture was diluted with water (30 mL) and extracted with ethyl acetate (30 mL×3). The organic layers were dried over sodium sulfate and concentrated in vacuum. The crude product was purified by column chromatography (petroleum ether/ethyl acetate=5/1). The product fractions were collected and the solvent was evaporated to give intermediate C', 0.16 g, 32%.

Preparation of Intermediate D'

To a solution of intermediate C' (120 mg, 0.48 mmol) in ammonia 4M in MeOH (15 mL) was added Raney Ni (50 mg) under N2. The suspension was degassed under vacuum and purged with H$_2$ several times. The mixture was stirred under H$_2$ (15 psi) at 25° C. for 10 hours. The suspension was filtered through a pad of Celite® and the pad was washed with methanol (20 mL). The combined filtrates were concentrated in vacuum to give intermediate D', 0.12 g, 98%.

Preparation of Compound 5

To a solution of 2-ethyl-5H,6H,7H,8H-imidazo[1,2-a]pyridine-3-carboxylic acid CAS [1529528-99-1], 0.226 g, 0.53 mmol, purity=45%) in DMF (10 mL) was added intermediate D' (0.12 g, 0.476 mmol), HATU (217.01 mg, 0.57 mmol) and diisopropylethylamine (0.184 g, 1.43 mmol). The mixture was stirred at room temperature overnight. The mixture was diluted with water (20 mL) and extracted with dichloromethane (10 mL×3). The organic layers were dried over sodium sulfate, filtered and concentrated in vacuum. The residue was purified by high performance liquid chromatography (Waters Xbridge Prep OBD C18 150×30 5μ, 25 ml/min, mobile phase: water (containing 0.05% $NH_3.H_2O$)/Acetonitrile, 50/50). The desired fraction was collected and evaporated to remove off acetonitrile in vacuum. The residue was lyophilized to give Compound 5, 0.055 g, 27%.

$^1$H NMR (400 MHz, CHLOROFORM-d) δ=7.22 (d, J=8.4 Hz, 2H), 6.62 (d, J=8.8 Hz, 2H), 5.83 (br. s., 1H), 4.50 (d, J=5.3 Hz, 2H), 4.23 (t, J=6.0 Hz, 2H), 3.43 (t, J=7.7 Hz, 2H), 3.25 (dd, J=2.6, 9.7 Hz, 2H), 2.97 (br. s., 2H), 2.86 (t, J=6.4 Hz, 2H), 2.68 (q, J=7.5 Hz, 2H), 2.52-2.35 (m, 2H), 2.15-2.02 (m, 2H), 1.98-1.85 (m, 4H), 1.24 (t, J=7.5 Hz, 3H).

Compound 6

Synthesis of Compound 6

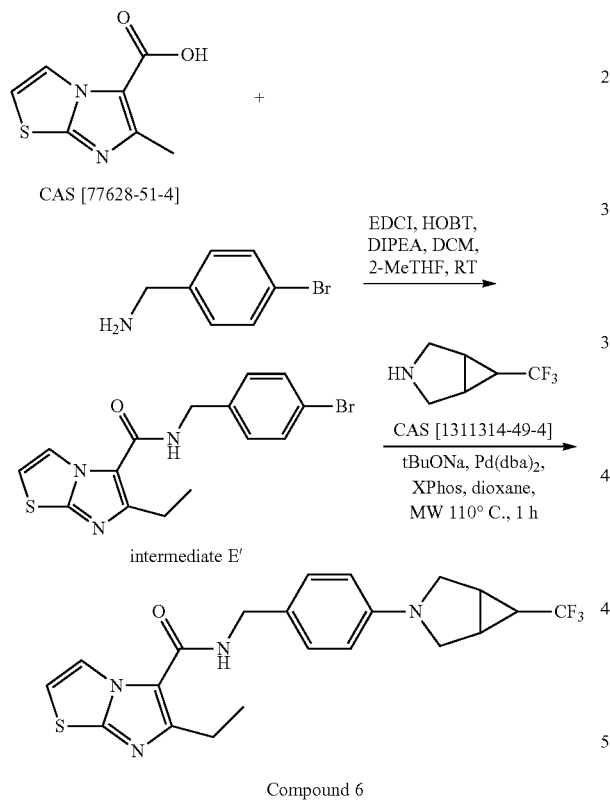

Compound 6

Preparation of Intermediate E'

A solution of 6-Methylimidazo[2,1-B][1,3]thiazole-5-carboxylic acid (CAS [77628-51-4], 1.96 g, 10.75 mmol), 4-Bromobenzylamine (CAS [3959-07-7], 2.4 g, 12.9 mmol), EDCI.HCl (1.67 g, 10.75 mmol), HOBT (1.45 g, 10.75 mmol) and diisopropylethylamine (1.85 mL, 10.75 mmol) in DCM (40 mL) and THF (40 mL) was stirred at room temperature overnight. Water and DCM were added. The organic layer was separated with an hydrophobic frit and evaporated. EtOH (20 mL) was added and the residue was stirred for 30 min at room temperature. The precipitate was filtered off and dried under vacuum to give intermediate E' as a pale beige powder, 1.78 g, 47%.

Preparation of Compound 6

A mixture of intermediate E' (0.2 g, 0.57 mmol), 6-(trifluoromethyl)-3-azabicyclo-[3.1.0]hexane hydrochloride (CAS [1311314-49-4], 0.13 g, 0.69 mmol), sodium tert-butoxide (0.16 g, 1.71 mmol) and Xphos (0.033 g, 0.057 mmol) in F (4.2 mL) was purged with N2 flow for 5 min under stirring. Then Pd(dba)$_2$ (0.026 g, 0.029 mmol) was added and the solution was heated at 100° C. overnight. The mixture was poured out into water, extracted with EtOAc, the mixture was filtered through a short pad of Celite®, the organic layer was separated, washed with water and brine, dried (MgSO$_4$) and evaporated till dryness, 0.245 g.

DIPE (25 mL) was added and the residue was triturated and stirred at room temperature for 30 min. The precipitate was filtered off and dried under vacuum at 60° C. to give a pale beige powder, 0.190 g.

A purification was performed via Reverse phase (Stationary phase: X-Bridge-C18 5 μm 30×150 mm, Mobile phase: Gradient from 65% NH$_4$HCO$_3$ 0.5%, 35% ACN to 25% NH$_4$HCO$_3$ 0.5%, 75% ACN). Pure fractions were collected and evaporated to give, 0.095 g, 39%.

The residue was crystallized from DIPE, filtered off and dried under vacuum at 60° C. affording Compound 6 as a white powder, 0.084 g, 35%.

1H NMR (500 MHz, DMSO-d6) δ ppm 8.05 (d, J=4.4 Hz, 1H) 8.02 (t, J=6.0 Hz, 1H) 7.31 (d, J=4.4 Hz, 1H) 7.16 (d, J=8.5 Hz, 2H) 6.55 (d, J=8.5 Hz, 2H) 4.35 (d, J=5.7 Hz, 2H) 3.62 (d, J=9.5 Hz, 2H) 3.15 (br d, J=9.1 Hz, 2H) 2.47 (s, 3H) 2.17 (br s, 2H) 1.73-1.83 (m, 1H)

Compound 7

Synthesis of Compound 7

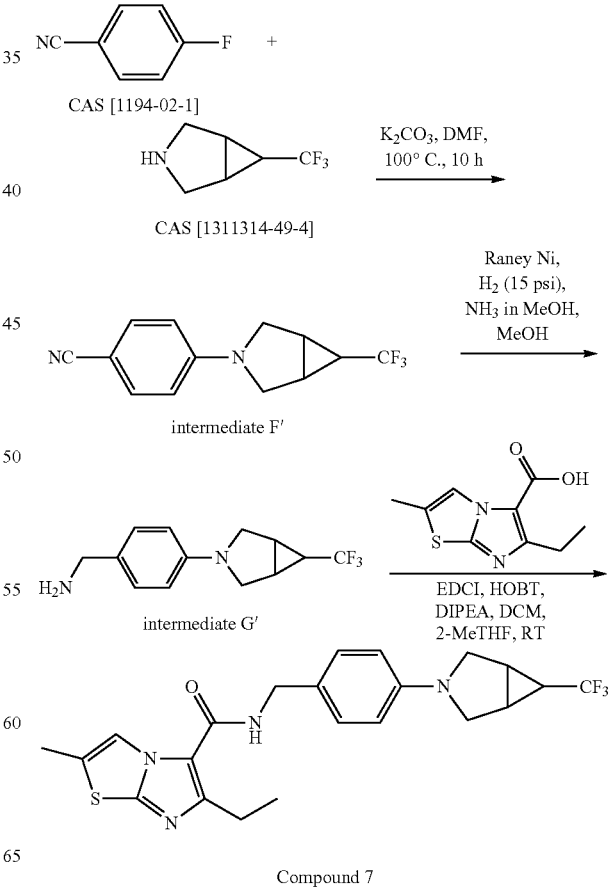

Compound 7

Preparation of Intermediate F'

A solution of 6-(trifluoromethyl)-3-azabicyclo[3.1.0] hexane hydrochloride (CAS [1311314-49-4], 0.5 g, 2.67 mmol), 4-Fluorobenzonitrile (CAS [1194-02-1], 0.27 g, 2.22 mmol) and potassium carbonate (0.46 g, 3.33 mmol) in DMF (4.3 mL) was heated at 110° C. for 18 hours. The solution was cooled down to room temperature. Water and EtOAc were added. The organic layer was extracted, dried over MgSO$_4$, filtered and evaporated. Purification was carried out by flash chromatography over silica gel (Irregular SiOH, 15-35 μm, 40 g, Heptane/EtOAc 70/30). Pure fractions were collected and evaporated to give intermediate F' as a white powder, 0.214 g, 38%.

Preparation of Intermediate G'

Lithium Aluminium hydride 1M in THF (3.39 mL, 3.39 mmol) was slowly added dropwise to a solution of intermediate F' (0.21 g, 0.85 mmol) in THF (7.9 mL) cooled in a ice bath at 5° C. The solution was stirred 1 hour at 5° C. after the addition and then the mixture was stirred at room temperature for 2 hours. The solution was cooled down to 0° C. and then a solution of THF/H$_2$O (90/10) was slowly added dropwise. The mixture was filtered off throught a pad of Celite® and washed with EtOAc. The organic layer was separated, dried (MgSO$_4$), filtered and evaporated affording intermediate G' as a white powder, 0.215 g, 94%.

Preparation of Compound 7

A solution of 6-Ethyl-2-imidazo[2,1b]thiazole-5-carboxylic acid (CAS [1131613-58-5], 0.11 g, 0.52 mmol), intermediate G' (0.17 g, 0.63 mmol), EDCI.HCl (0.1 g, 0.52 mmol), HOBT (0.08 g, 0.52 mmol) and diisopropylethylamine (0.18 mL, 1.05 mmol) in DCM (3.8 mL) and 2-MeTHF (10 mL) was stirred at room temperature overnight. Water and DCM were added. The organic layer was washed with water, dried over MgSO4, filtered and evaporated. Purification was carried out by flash chromatography over silica gel (Irregular SiOH 15-35 μm, 40 g, CH$_2$Cl$_2$/CH$_3$OH/NH$_4$OH from 100/0/0 to 97/3/0.1). Pure fractions were evaporated to give 0.184 g. The residue was crystallized from DIPE, filtered off and dried under vacuum at 60° C. affording Compound 7, 0.169 g, 72%.

1H NMR (500 MHz, DMSO-d6) δ ppm 8.01 (t, J=6.0 Hz, 1H) 7.87 (d, J=1.6 Hz, 1H) 7.15 (d, J=8.5 Hz, 2H) 6.55 (d, J=8.8 Hz, 2H) 4.34 (d, J=6.0 Hz, 2H) 3.62 (d, J=9.5 Hz, 2H) 3.14 (br d, J=9.1 Hz, 2H) 2.83 (q, J=7.6 Hz, 2H) 2.41 (d, J=1.3 Hz, 3H) 2.17 (br s, 2H) 1.75-1.84 (m, 1H) 1.19 (t, J=7.6 Hz, 3H)

The following compounds were also prepared in accordance with the procedures described herein:

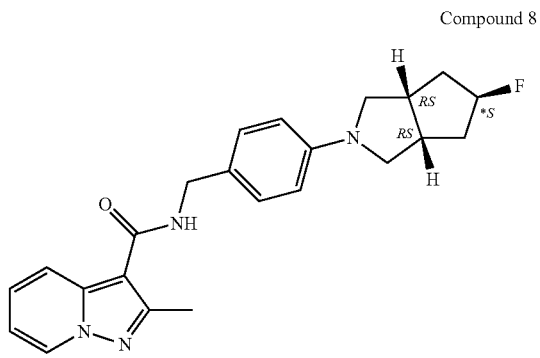

Compound 8

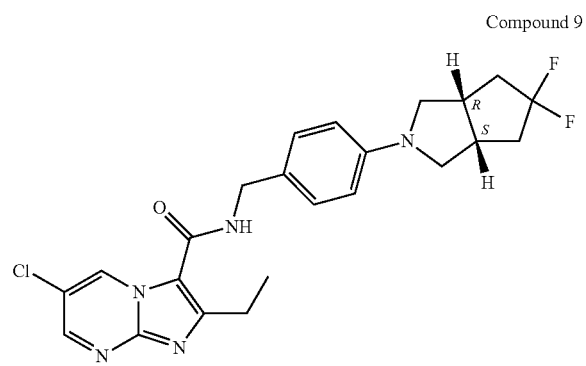

Compound 9

Characterising Data Table

| Compound No | Meting Point (Kofler or DSC) | LCMS Rt | UV Area % | MW exact | BPM1/ BPM2 | LCMS Method |
|---|---|---|---|---|---|---|
| Cpd 1 | | 3.14 | 96.8 | 440.2 | 441.1 | Method C |
| Cpd 6 | 222° C. (Kofler) | 2.99 | 98.8 | 420.1 | 421/419 | Method A |
| Cpd 7 | 230° C. (Kofler) | 3.26 | 100.0 | 448.2 | 449/417 | Method A |
| Cpd 4 | | 3.54 | 99.7 | 441.2 | 442.1 | Method C |
| Cpd 2 | | 4.49 | 95.3 | 426.2 | 427.2 | Method B |
| Cpd 3 | | 2.86 | 98.7 | 410.2 | 411.2 | Method C |
| Cpd 5 | | 3.06 | 99.7 | 428.2 | 429.2 | Method C |
| Cpd 8 | 173.10/−76.63 Jg^−1, 25° C. to 300° C./10° C. min/40 μl Al | 2.91 | 98.8 | 392.2 | 393/451.2 [M + CH$_3$COO]$^-$ | Method A |
| Cpd 9 | 207.51° C./−87.87 Jg^−1, 25° C. to 350° C./10° C. min/40 μl Al (DSC: 25° C. to 350° C./10° C. min/40 μl Al) | 3.12 | 97.7 | 459.2 | 460/458.2 | Method A |

Analytical Methods

LCMS

The mass of some compounds was recorded with LCMS (liquid chromatography mass spectrometry). The methods used are described below.

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl . . . ), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector.

TABLE

LCMS Method codes (Flow expressed in mL/min; column temperature (T) in ° C.; Run time in minutes).

| Method code | Instrument | Column | Mobile phase | gradient | Flow Column T | Run time |
|---|---|---|---|---|---|---|
| Method A | Waters: Acquity UPLC ® - DAD and Quattro Micro ™ | Waters: BEH C18 (1.7 μm, 2.1 × 100 mm) | A: 95% CH$_3$COONH$_4$ 7 mM/5% CH$_3$CN, B: CH$_3$CN | 84.2% A for 0.49 min, to 10.5% A in 2.18 min, held for 1.94 min, back to 84.2% A in 0.73 min, held for 0.73 min. | 0.343 40 40 | 6.2 |

Hereinafter, "MSD" Mass Selective Detector, "DAD" Diode Array Detector.

TABLE

LCMS Method codes (Flow expressed in mL/min; column temperature (T) in ° C.; Run time in minutes).

| Method Code | Instrument | Column | Mobile phase | gradient | Flow Column T | Run time |
|---|---|---|---|---|---|---|
| Method B | Agilent: 1100/1200 - DAD and MSD | Agilent: TC-C18 (5 μm, 2.1 × 50 mm) | A: CF$_3$COOH 0.1% in water, B: CF$_3$COOH 0.05% in CH$_3$CN | 100% A for 1 min, to 40% A in 4 min, to 15% A in 2.5 min, back to 100% A in 2 min. | 0.8 50 | 10.5 |
| Method C | Agilent: 1100/1200 - DAD and MSD | Agilent: TC-C18 (5 μm, 2.1 × 50 mm) | A: CF$_3$COOH 0.1% in water, B: CF$_3$COOH 0.05% in CH$_3$CN | 90% A for 0.8 min, to 20% A in 3.7 min, held for 3 min, back to 90% A in 2 min. | 0.8 50 50 | 10.5 |

Pharmacological Examples

MIC Determination for Testing Compounds Against *M. tuberculosis*.

Test 1

Appropriate solutions of experimental and reference compounds were made in 96 well plates with 7H9 medium. Samples of *Mycobacterium tuberculosis* strain H37Rv were taken from cultures in logarithmic growth phase. These were first diluted to obtain an optical density of 0.3 at 600 nm wavelength and then diluted 1/100, resulting in an inoculum of approximately 5×10 exp5 colony forming units per well. Plates were incubated at 37° C. in plastic bags to prevent evaporation. After 7 days, resazurin was added to all wells. Two days later, fluorescence was measured on a Gemini EM Microplate Reader with 543 excitation and 590 nm emission wavelengths and $MIC_{50}$ and/or $pIC_{50}$ values (or the like, e.g. $IC_{50}$, $IC_{90}$, $pIC_{90}$, etc) were (or may be) calculated.

Test 2

Round-bottom, sterile 96-well plastic microtiter plates are filled with 100 μl of Middlebrook (1×) 7H9 broth medium. Subsequently, an extra 100 μl medium is added to column 2. Stock solutions (200× final test concentration) of compounds are added in 2 μl volumes to a series of duplicate wells in column 2 so as to allow evaluation of their effects on bacterial growth. Serial 2-fold dilutions are made directly in the microtiter plates from column 2 to 11 using a multipipette. Pipette tips are changed after every 3 dilutions to minimize pipetting errors with high hydrophobic compounds. Untreated control samples with (column 1) and without (column 12) inoculum are included in each microtiter plate. Approximately 10000 CFU per well of *Mycobacterium tuberculosis* (strain H37RV), in a volume of 100 μl in Middlebrook (1×) 7H9 broth medium, is added to the rows A to H, except column 12. The same volume of broth medium without inoculum is added to column 12 in row A to H. The cultures are incubated at 37° C. for 7 days in a humidified atmosphere (incubator with open air valve and continuous ventilation). On day 7 the bacterial growth is checked visually.

The 90% minimal inhibitory concentration ($MIC_{90}$) is determined as the concentration with no visual bacterial growth.

Test 3: Time Kill Assays

Bactericidal or bacteriostatic activity of the compounds can be determined in a time kill assay using the broth dilution method. In a time kill assay on *Mycobacterium tuberculosis* (strain H37RV), the starting inoculum of *M. tuberculosis* is $10^6$ CFU/ml in Middlebrook (1×) 7H9 broth. The antibacterial compounds are used at the concentration of 0.1 to 10 times the $MIC_{90}$. Tubes receiving no antibacterial agent constitute the culture growth control. The tubes containing the microorganism and the test compounds are incubated at 37° C. After 0, 1, 4, 7, 14 and 21 days of incubation samples are removed for determination of viable counts by serial dilution (10'- to 10') in Middlebrook 7H9 medium and plating (100 μl) on Middlebrook 7H11 agar. The plates are incubated at 37° C. for 21 days and the number of colonies are determined. Killing curves can be constructed by plotting the $\log_{10}$ CFU per ml versus time. A bactericidal effect is commonly defined as 3-$\log_{10}$ decrease in number of CFU per ml as compared to untreated inoculum. The potential carryover effect of the drugs is removed by serial dilutions and counting the colonies at highest dilution used for plating.

Test 4 (See Also Test 1 Above; in this Test a Different Strain of *Mycobacterium tuberculosis* Strain is Employed)

Appropriate solutions of experimental and reference compounds were made in 96 well plates with 7H9 medium. Samples of *Mycobacterium tuberculosis* strain EH 4.0 (361.269) were taken from cultures in stationary growth phase. These were first diluted to obtain an optical density of 0.3 at 600 nm wavelength and then diluted 1/100, resulting in an inoculum of approximately 5×10 exp5 colony forming units per well. Plates were incubated at 37° C. in plastic bags to prevent evaporation. After 7 days, resazurin was added to all wells. Two days later, fluorescence was measured on a Gemini EM Microplate Reader with 543 nm excitation and 590 nm emission wavelengths and MIC50 and/or pIC50 values (or the like, e.g. IC50, IC90, pIC90, etc) were (or may be) calculated. $pIC_{50}$ values may be recorded below in μg/mL.

Results

Compounds of the invention/examples, for example when tested in Test 1 or Test 2 decribed above, may typically have an $IC_{90}$ value from 0.01 to 10 μg/ml. Compounds of the invention/examples, for example when tested in Test 1 or Test 2 described above, may typically have a $pIC_{50}$ from 3 to 10 (e.g. from 4.0 to 9.0, such as from 5.0 to 8.0)

Compounds of the examples were tested in Test 1 described above (in section "Pharmacological Examples") and the following results were obtained:

Biological Data Table

Compounds of the examples were tested in Test 4 described above (in section "Pharmacological Examples") and the following results were obtained:

| Compound No | $pIC_{50}$ |
|---|---|
| Cpd 1 | 7.4 |
| Cpd 6 | 7 |
| Cpd 7 | 7.5 |
| Cpd 4 | 6.95 |
| Cpd 2 | 7.3 |
| Cpd 3 | 7 |
| Cpd 5 | 7.1 |
| Cpd 8 | 5.95 |
| Cpd 9 | 7.8 |

The invention claimed is:

1. A compound of formula (I)

(I)

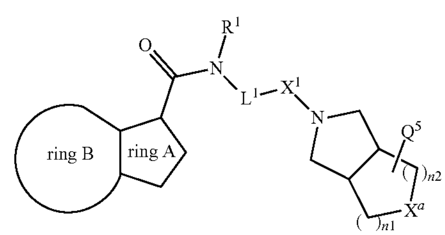

or a pharmaceutically acceptable salt thereof wherein $R^1$ represents $C_{1-6}$ alkyl or hydrogen;

$L^1$ represents a linker group —$C(R^a)(R^b)$—;

$X^1$ represents an optional carbocyclic aromatic linker group, which linker group may itself be optionally substituted by one or more substituents selected from fluoro, —OH, —$OC_{1-6}$ alkyl and $C_{1-6}$ alkyl, wherein the latter two alkyl moieties are themselves optionally substituted by one or more fluoro atoms;

n1 and n2 independently represent 0 or 1;
$R^a$ and $R^b$ independently represent hydrogen or $C_{1-6}$ alkyl optionally substituted by one or more fluoro atoms;
$X^a$ represents or —C($R^{a1}$)($R^{b1}$)$_m$— or —N($R^{c1}$)—;
m represents 1;
each $R^{a1}$ and $R^{b1}$ independently represents fluoro, hydrogen or $C_{1-6}$ alkyl;
$R^{c1}$ represents hydrogen or $C_{1-6}$ alkyl;
$Q^5$ represents one or more independent substituents selected from: halo; $C_{1-6}$ alkyl optionally substituted by one or more halo; —$OC_{1-6}$ alkyl optionally substituted by one or more halo; aryl; and heteroaryl, which latter two aromatic groups may themselves be optionally substituted by one or more substituents selected from halo, $C_{1-6}$ alkyl and —$OC_{1-6}$ alkyl, which latter two alkyl moieties may themselves be substituted with one or more fluoro atoms;
ring A is a 5-membered aromatic ring containing at least one heteroatom;
ring B is a 5- or 6-membered ring, which may be aromatic or non-aromatic, optionally containing one to four heteroatoms;
either ring A and/or ring B may be optionally substituted by one or more substituents selected from: halo, $C_{1-6}$ alkyl optionally substituted by one or more halo atoms or —$OC_{1-6}$alkyl optionally substituted by one or more fluoro atoms.

2. The compound as claimed in claim 1, wherein:
$R^1$ represents hydrogen;
$R^a$ and $R^b$ independently represent hydrogen; and/or
$L^1$ represents —$CH_2$—.

3. The compound as claimed in claim 1, wherein $X^1$ represents a carbocyclic aromatic linker group that is:
-phenylene-: or

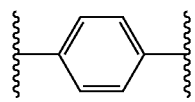

-naphthylene;

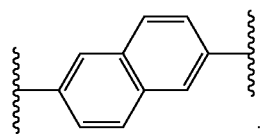 [SMILES: *c1ccc2cc(*)ccc2c1]

4. The compound as claimed in claim 1, wherein:
$X^a$ represents —$CH_2$— which is substituted by one or more $Q^5$ substituents; and/or
$Q^5$ represents halo.

5. The compound as claimed in claim 1 wherein:
ring A is represented as follows:

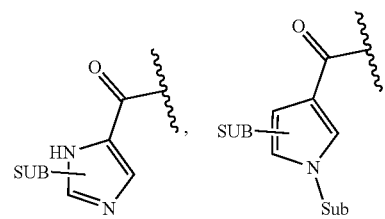

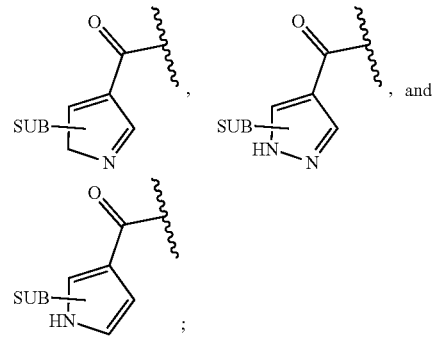

and/or
ring B is represented as follows:

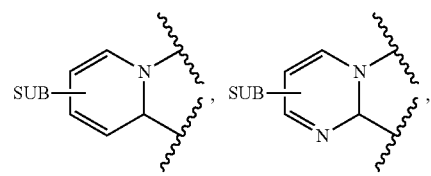

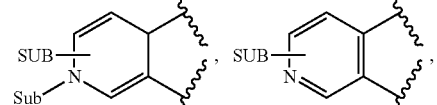

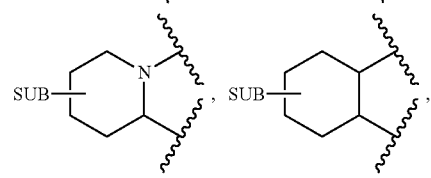

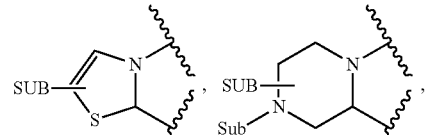

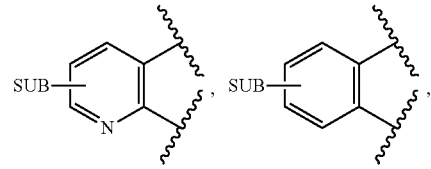

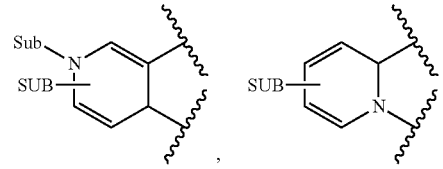

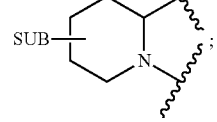

wherein "SUB" and "Sub" represent one or more possible substituents on the relevant atom.

6. The compound as claimed in claim 1, wherein the combined ring systems Ring A and Ring B may be represented as follows:

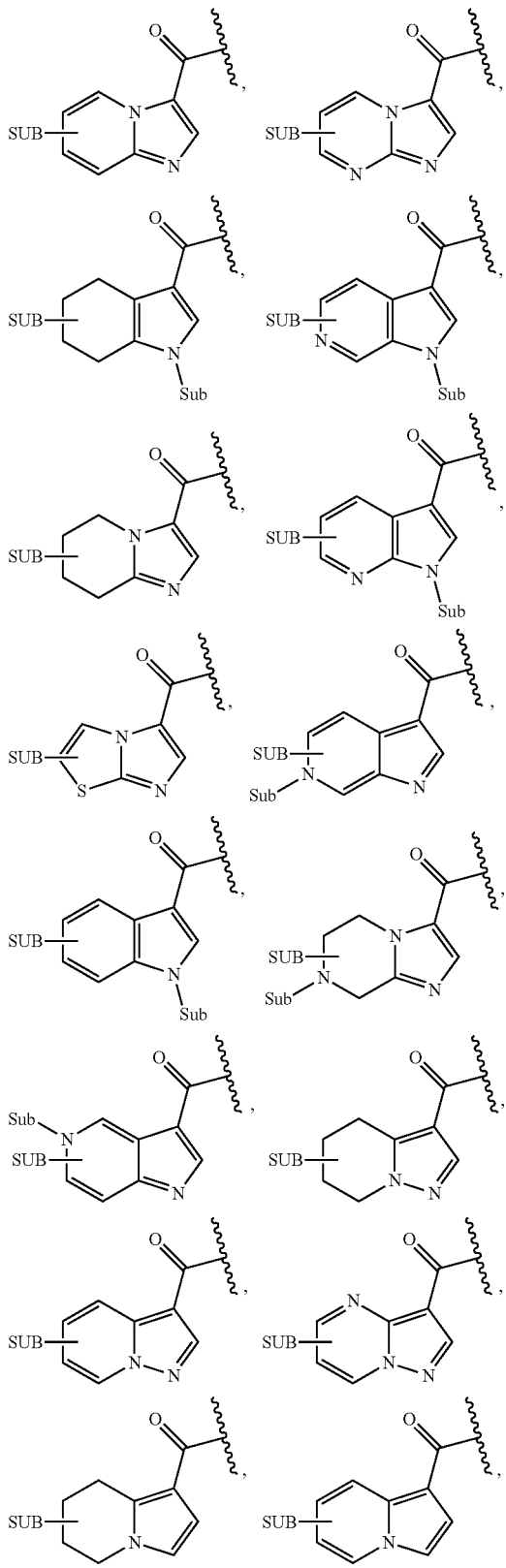

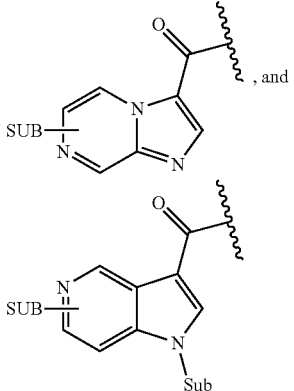

where "SUB" represents one or more possible substituents on the bicycle and "Sub" represents a possible optional substituent on the N atom of the bicycle.

7. The compound of formula (I) as defined in claim 1 wherein:
   $L^1$ represents —CH$_2$—;
   $X^a$ represents —CH$_2$— and which is substituted by one or two $Q^5$ substituent(s).

8. The compound as claimed in claim 7, wherein:
   $Q^5$ represents halo or C$_{1-3}$ alkyl optionally substituted by one or more fluoro atoms;
   one or two $Q^5$ substituents are only present on V.

9. The compound as claimed in claim 7, wherein:
   ring A and ring B together represent a 8 or 9-membered bicyclic ring containing at least one nitrogen atom wherein at least one nitrogen atom is common to both rings;
   optional substituents on ring A and ring B are halo, C$_{1-3}$ alkyl and —OC$_{1-3}$ alkyl.

10. A pharmaceutical composition comprising a pharmaceutically acceptable carrier and, as active ingredient, a therapeutically effective amount of a compound as defined in claim 7.

11. A method for treating a patient suffering from tuberculosis, said method comprising administering to said patient a therapeutically effective amount of a compound of formula (I) as defined in claim 1.

12. A method of treatment of a bacterial infection, which method comprises administration of a therapeutically effective amount of a compound according to claim 1.

13. A combination of (a) a compound according to claim 1, and (b) one or more other anti-tuberculosis agent.

14. A product containing (a) a compound according to claim 1, and (b) one or more other anti-tuberculosis agent, as a combined preparation for simultaneous, separate or sequential use in the treatment of a bacterial infection.

15. The compound as claimed in claim 2, wherein X' represents a carbocyclic aromatic linker group that is:
   -phenylene-: or

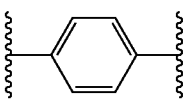 [SMILES: *c1ccc(*)cc1]

-naphthylene:

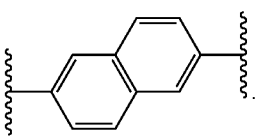

16. The compound as claimed in claim 1, wherein $X^1$ is absent.

17. The compound as claimed in claim 2, wherein $X^1$ is absent.

18. The compound as claimed in claim 2, wherein:
$X^a$ represents —$CH_2$— which is substituted by one or more $Q^5$ substituents; and/or
$Q^5$ represents halo.

19. The compound as claimed in claim 3, wherein:
$X^a$ represents —$CH_2$— which is substituted by one or more $Q^5$ substituents; and/or
$Q^5$ represents halo.

20. The compound as claimed in claim 15, wherein:
$X^a$ represents —$CH_2$— which is substituted by one or more $Q^5$ substituents; and/or
$Q^5$ represents halo.

21. The compound as claimed in claim 16, wherein:
$X^a$ represents —$CH_2$— which is substituted by one or more $Q^5$ substituents; and/or
$Q^5$ represents halo.

22. The compound as claimed in claim 17, wherein:
$X^a$ represents —$CH_2$— which is substituted by one or more $Q^5$ substituents; and/or
$Q^5$ represents halo.

\* \* \* \* \*